US006858772B2

(12) United States Patent
Allen

(10) Patent No.: US 6,858,772 B2
(45) Date of Patent: Feb. 22, 2005

(54) TRANSGENIC MICE CONTAINING MAGNESIUM-DEPENDENT PROTEIN PHOSPHATASE GENE DISRUPTIONS

(75) Inventor: Keith D. Allen, Cary, NC (US)

(73) Assignee: Deltagen, Inc., San Carlos, CA (US)

( * ) Notice: Subject to any disclaimer, the term of this patent is extended or adjusted under 35 U.S.C. 154(b) by 0 days.

(21) Appl. No.: 09/972,741

(22) Filed: Oct. 5, 2001

(65) Prior Publication Data

US 2002/0100070 A1 Jul. 25, 2002

Related U.S. Application Data

(63) Continuation-in-part of application No. 09/815,935, filed on Mar. 22, 2001.

(60) Provisional application No. 60/216,249, filed on Jul. 6, 2000, and provisional application No. 60/191,235, filed on Mar. 22, 2000.

(51) Int. Cl.[7] ....................... A01K 67/027; C12N 15/00

(52) U.S. Cl. ............................................ 800/18; 800/25

(58) Field of Search ................................ 800/18, 25, 3, 800/22

(56) References Cited

PUBLICATIONS

Campbell and Wilmut. Totipotency or Multipotency of Cultured Cells: Applications and Progress. Theriogenology. Jan. 1, 1997. vol. 47, No. 1, pp. 63–70.*

Jacks et al. Effects of an Rb mutation in the mouse. Sep. 24, 1992. Nature. vol. 359, pp. 295–300.*

Bradley et al. Modifying the Mouse: Design and Desire. May 1992. Biotechnology. vol. 10, pp. 534–539.*

Mullins and Mullins. Perspective Series: Molecular Medicine in Genetically Engineered Animals. Apr. 1, 1996. Clinical Investigation. vol. 97, No. 7, pp. 1557–1560.*

Sigmund. Viewpoint: Are Studies in Genetically Altered mice Out of Control? Jun. 2000. Arterioscler Thromb. Vasc. Biol. vol. 20. pp. 1425–1429.*

Wall. Transgenic Livestock: Progress and Prospects for the Future. 1996. Theriogenology. vol. 45, pp. 57–68.*

Mansour et a., Disruption of the proto–oncogene int–2 in mouse embryo–derived stem cells: a general strategy for targeting mutations to non–selectable genes, 1988, Nature, vol. 336, pp. 348–352.*

Travis et al., Protein phosphate 2C dephosphorylates and inactivates cystic fibrosis transmembrane conductance regulator, 1997, PNAS, vol. 94, pp. 11055–11060.*

Kato et al., The cDNA sequence encoding mouse Mg2+ dependent protein phosphatase alpha, 1994, Gene, vol. 145, pp. 311–312.*

* cited by examiner

*Primary Examiner*—Anne-Marie Falk
*Assistant Examiner*—Celine Qian
(74) *Attorney, Agent, or Firm*—Robert J. Driscoll

(57) ABSTRACT

The present invention relates to transgenic animals, as well as compositions and methods relating to the characterization of gene function. Specifically, the present invention provides transgenic mice comprising mutations in the magnesium-dependent protein phosphatase gene. Such transgenic mice are useful as models for disease and for identifying agents that modulate gene expression and gene function, and as potential treatments for various disease states and disease conditions.

7 Claims, 3 Drawing Sheets

CCCGGGCCCGGCCGCCGTCGCGGACCCCGTGCCCGGCCGCCGTCGCCACCGCCGCCCCGGCCGACCGAG
GGACCCGCCCGCCCGCGGCTGCTCCGGACCTAGAGGATCAAGTCATAATGGGAGCATTTTTAGACAAGCC
AAAGATGGAGAAGCATAATGCCCAGGGGCAGGGGAATGGGTTACGATACGGCCTAAGCAGCATGCAAGGT
TGGCGAGTTGAAATGGAGGACGCACACACGGCTGTGATCGGTTTGCCAAGTGGACTTGAGACATGGTCAT
TCTTTGCTGTATATGATGGGCATGCTGGTTCTCAGGTTGCCAAATACTGCTGTGAGCACTTGTTAGATCA
CATCACCAATAACCAGGATTTCAGAGGATCTGCAGGAGCACCTTCTGTGGAGAACGTAAAGAATGGAATC
AGAACAGGGTTTCTGGAGATTGATGAACACATGAGAGTTATGTCAGAGAAGAAACATGGTGCAGATAGAA
GCGGGTCAACAGCTGTGGGCGTCTTAATCTCTCCCCAACATACTTATTTCATTAACTGTGGAGACTCGAG
AGGTTTACTTTGTAGGAATAGAAAAGTTCACTTCTTCACACAAGACCATAAACCAAGTAACCCGCTGGAA
AAAGAACGAATTCAGAATGCAGGGGGCTCGGTGATGATTCAGCGTGTCAATGGCTCTCTGGCTGTATCGA
GGGCCCTTGGGGATTTCGATTACAAATGTGTCCATGGAAAAGGTCCCACAGAGCAGCTTGTCTCCCCAGA
GCCCGAAGTCCATGATATTGAAAGGTCTGAAGAAGATGACCAGTTCATCATCCTTGCATGCGATGGCATC
TGGGACGTCATGGGGAACGAAGAGCTCTGTGACTTTGTGAGATCCAGACTTGAAGTCACTGATGACCTTG
AGAAAGTTTGCAATGAAGTAGTCGACACCTGCTTGTATAAGGGAAGTCGAGACAACATGAGTGTGATTTT
GATCTGTTTTCCAAGTGCACCCAAAGTCTCGGCAGAGGCGGTGAAGAAGGAGGCGGAGCTGGACAAGTAC
CTGGAGAGCAGAGTAGAAGAAATCATAAAGAAGCAGGTGGAAGGCGTCCCTGACTTAGTCCACGTGATGC
GCACGTTAGCCAGTGAGAACATCCCCAGCCTCCCACCAGGGGGTGAATTGGCAAGCAAGCGGAATGTAAT
TGAAGCCGTTTACAATAGACTGAACCCTTACAAAAATGACGACACTGATTCTGCGTCAACCGATGATATG
TGGTAAAGCCGCTCACCCAGCCGTGGACTCACCTTCGCCTGCAAAGGGGAAGCCAGCTCATCCTTGCCGA
GCCTTTACCATCCATCACCGACTTCACAGGAGGGTCTGACACGGGTGAGGACTGCAG (SEQ NO:1)

MGAFLDKPKMEKHNAQGQGNGLRYGLSSMQGWRVEMEDAHTAVIGLPSGLE
TWSFFAVYDGHAGSQVAKYCCEHLLDHITNNQDFRGSAGAPSVENVKNGIRTG
FLEIDEHMRVMSEKKHGADRSGSTAVGVLISPQHTYFINCGDSRGLLCRNRKVH
FFTQDHKPSNPLEKERIQNAGGSVMIQRVNGSLAVSRALGDFDYKCVHGKGPT
EQLVSPEPEVHDIERSEEDDQFIILACDGIWDVMGNEELCDFVRSRLEVTDDLEK
VCNEVVDTCLYKGSRDNMSVILICFPSAPKVSAEAVKKEAELDKYLESRVEEIIK
KQVEGVPDLVHVMRTLASENIPSLPPGGELASKRNVIEAVYNRLNPYKNDDTDS
ASTDDMW (SEQ ID NO:2)

FIGURE 1 underlined = deleted in targeting construct

[ ] = sequence flanking Neo insert in targeting construct

CCCGGGCCCGGCCGCCGTCGCGGACCCCGTGCCCGGCCGCCGTCGCCACCGCCGCCCCG
GCCGACCGAGGGACCCGCCCGCCCGCGGCTGCTCCGG[ACCTAGAGGATCAAGTCATAATG
GGAGCATTTTTAGACAAGCCAAAGATGGAGAAGCATAATGCCC] AGGGGCAGGGGAATGGG
TTACGATACGGCCTAAGCAGCATGCAAGGTTGGCGAGTTGAAATGGAGGACGCACACACG
GCTGTGATCGGTTTGCCAAGTGGACTTGAGACATGGTCATTCTTTGCTGTATATGATGGG
CATGCTGGTTCTCAGGTTGCCAAATA[CTGCTGTGAGCACTTGTTAGATCACATCACCAAT
AACCAGGATTTCAGAGGATCTGCAGGAGCACCTTCTGTGGAGAACGTAAAGAATGGAATC
AGAACAGGGTTTCTGGAGATTGATGAACACATGAGAGTTATGTCAGAGAAGAAACATGGT
GCAGATAGAAGCGGGTCAACAGCTGTGGGCGTCTTAATCTCTCCCCAACATACTTATTTC
ATTAACTGTGGAGACTCGAGAGGTTTACTTTGTAGGAATAGAAAAGTTCACTTCTTCACA
CAAGACCATAAACCAAGTAACCCGCTGGAAAAAGAACGAATTCAGAATGCAGGGGGCTCG
GTGATGATTCAGCGTGTCAATGGCTCTCTGGCTGTATCGAGGGCCCTTGGGGATTTCGAT
TACAAATGTGTCCATGG] AAAAGGTCCCACAGAGCAGCTTGTCTCCCCAGAGCCCGAAGTC
CATGATATTGAAAGGTCTGAAGAAGATGACCAGTTCATCATCCTTGCATGCGATGGCATC
TGGGACGTCATGGGGAACGAAGAGCTCTGTGACTTTGTGAGATCCAGACTTGAAGTCACT
GATGACCTTGAGAAAGTTTGCAATGAAGTAGTCGACACCTGCTTGTATAAGGGAAGTCGA
GACAACATGAGTGTGATTTTGATCTGTTTTCCAAGTGCACCCAAAGTCTCGGCAGAGGCG
GTGAAGAAGGAGGCGGAGCTGGACAAGTACCTGGAGAGCAGAGTAGAAGAAATCATAAAG
AAGCAGGTGGAAGGCGTCCCTGACTTAGTCCACGTGATGCGCACGTTAGCCAGTGAGAAC
ATCCCCAGCCTCCCACCAGGGGGTGAATTGGCAAGCAAGCGGAATGTAATTGAAGCCGTT
TACAATAGACTGAACCCTTACAAAAATGACGACACTGATTCTGCGTCAACCGATGATATG
TGGTAAAGCCGCTCACCCAGCCGTGGACTCACCTTCGCCTGCAAAGGGGAAGCCAGCTCA
TCCTTGCCGAGCCTTTACCATCCATCACCGACTTCACAGGAGGGTCTGACACGGGTGAGG
ACTGCAG

FIGURE 2A

Gene Sequence Structure *

Size of full-length cDNA: 1387 bp 164 bp Sequence Deleted 326 bp

Targeting Vector* (genomic sequence)

Construct Number: 2639

Arm Length:
5': 2.5 kb
3': 4 kb

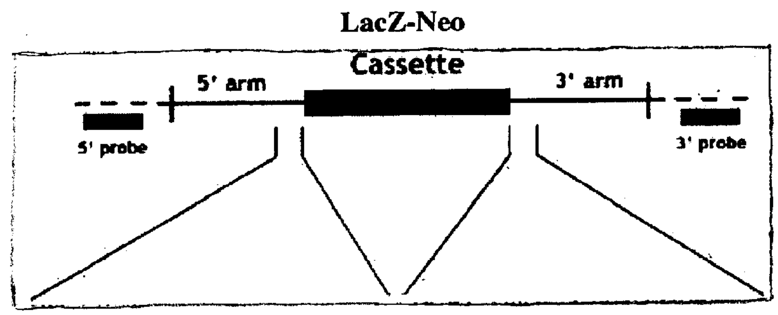

| | |
|---|---|
| 5'>GCAACACAATGCTTGTAGGTATAGCCTGTGAGTTTTTCCAGCTTCCTTGTATCTTATAGATTCTGGGTAAAGAGTGTTGGACATGTTTTGTTTCAAAGGCAATCACTTATTTTCTTATTTCTCTTCCTTTACAGACCTAGAGGATCAAGTCATAATGGGAGCATTTTTAGACAAGCCAAAGATGGAGAAGCATAATGCCC<3' (SEQ ID NO:3) | 5'>CTGCTGTGAGCACTTGTTAGATCACATCACCAATAACCAGGATTTCAGAGGATCTGCAGGAGCACCTTCTGTGGAGAACGTAAAGAATGGAATCAGAACAGGGTTTCTGGAGATTGATGAACACATGAGAGTTATGTCAGAGAAGAAACATGGTGCAGATAGAAGCGGGTCAACAGCTGTGGGCGTCTTAATCTCTCCCC<3' (SEQ ID NO:4) |

Targeting Vector
Endogenous Locus

* Not drawn to scale

FIGURE 2B

TRANSGENIC MICE CONTAINING MAGNESIUM-DEPENDENT PROTEIN PHOSPHATASE GENE DISRUPTIONS

RELATED APPLICATIONS

This application is a continuation-in-part of U.S. Utility application Ser. No. 09/815,935, filed Mar. 22, 2001, which claims priority to U.S. Provisional Application No. 60/191,235, filed Mar. 22, 2000; and U.S. Provisional Application No. 60/216,249, filed Jul. 6, 2000.

FIELD OF THE INVENTION

The present invention relates to transgenic animals, compositions and methods relating to the characterization of gene function.

BACKGROUND OF THE INVENTION

Phosphatases represent unique and attractive targets for small-molecule inhibition and pharmacological intervention. The protein phosphorylation/dephosphorylation cycle is one of the major regulatory mechanisms employed by eukaryotic cells to control cellular activities including growth and differentiation, cell-to-cell contacts, the cell cycle, and oncogenesis. It is estimated that more than 10% of the active proteins in a typical mammalian cell are phosphorylated. During protein phosphorylation or dephosphorylation, phosphate groups are transferred from adenosine triphosphate (ATP) molecules to a protein by protein kinases and are removed from the protein by protein phosphatases.

Since nearly all forms of human neoplasias have altered cell cycle control, the role of phosphatases in cell cycle control makes these molecules attractive targets for pharmaceutical intervention. The ability of phosphatase inhibitors to interfere with aberrant cell activity has been demonstrated. For example, the naturally occurring serine/threonine phosphatase inhibitor okadaic acid has been shown to induce apoptosis in myeloid leukemia cells (*J. Cell. Physiol.* 150, 484 (1992)) and in rat hepatocytes, rat pituitary adenoma cell, human mammary carcinoma cells and human neuroblastoma cells (*Exp. Cell Res.* 195, 237 (1991)).

Magnesium-dependent protein phosphatases appear to participate in a wide variety of functions including regulating cAMP-activated protein-kinase activity, $Ca^{2+}$-dependent signal transduction, tRNA splicing, and signal transmission related to heat shock responses. It was reported that the complete cDNA sequence encoding PP2C, alpha isoform (or PP2C-alpha) was cloned from mouse brain. PP2C-alpha (GI or NID Number: 532678; Accession Number: D28117) is a 1387 bp sequence that encodes a protein of 382 amino acids with a calculated molecular mass of 42,432 Da (*Gene* 145(2), 311–312 (1994)).

Given the importance of magnesium-dependent protein phosphatase in biological and disease processes, a clear need exists for further in vivo characterization, which may aid in the identification and discovery of therapeutics and treatments useful in preventing, ameliorating or correcting dysfunctions or diseases.

SUMMARY OF THE INVENTION

The present invention generally relates to transgenic animals, as well as to compositions and methods relating to the characterization of gene function.

The present invention provides transgenic cells comprising a disruption in the magnesium-dependent protein phosphatase gene. The transgenic cells of the present invention are comprised of any cells capable of undergoing homologous recombination. Preferably, the cells of the present invention are stem cells and more preferably, embryonic stem (ES) cells, and most preferably, murine ES cells. According to one embodiment, the transgenic cells are produced by introducing a targeting construct into a stem cell to produce a homologous recombinant, resulting in a mutation of the magnesium-dependent protein phosphatase gene. In another embodiment, the transgenic cells are derived from the transgenic animals described below. The cells derived from the transgenic animals includes cells that are isolated or present in a tissue or organ, and any cell lines or any progeny thereof.

The present invention also provides a targeting construct and methods of producing the targeting construct that when introduced into stem cells produces a homologous recombinant. In one embodiment, the targeting construct of the present invention comprises first and second polynucleotide sequences that are homologous to the magnesium-dependent protein phosphatase gene. The targeting construct also comprises a polynucleotide sequence that encodes a selectable marker that is preferably positioned between the two different homologous polynucleotide sequences in the construct. The targeting construct may also comprise other regulatory elements that may enhance homologous recombination.

The present invention further provides non-human transgenic animals and methods of producing such non-human transgenic animals comprising a disruption in the magnesium-dependent protein phosphatase gene. The transgenic animals of the present invention include transgenic animals that are heterozygous and homozygous for a mutation in the magnesium-dependent protein phosphatase gene. In one aspect, the transgenic animals of the present invention are defective in the function of the magnesium-dependent protein phosphatase gene. In another aspect, the transgenic animals of the present invention comprise a phenotype associated with having a mutation in the magnesium-dependent protein phosphatase gene.

The present invention also provides methods of identifying agents capable of affecting a phenotype of a transgenic animal. For example, a putative agent is administered to the transgenic animal and a response of the transgenic animal to the putative agent is measured and compared to the response of a "normal" or wild type mouse, or alternatively compared to a transgenic animal control (without agent administration). The invention further provides agents identified according to such methods. The present invention also provides methods of identifying agents useful as therapeutic agents for treating conditions associated with a disruption of the magnesium-dependent protein phosphatase gene.

The present invention further provides a method of identifying agents having an effect on magnesium-dependent protein phosphatase expression or function. The method includes administering an effective amount of the agent to a transgenic animal, preferably a mouse. The method includes measuring a response of the transgenic animal, for example, to the agent, and comparing the response of the transgenic animal to a control animal, which may be, for example, a wild-type animal or alternatively, a transgenic animal control. Compounds that may have an effect on magnesium-dependent protein phosphatase expression or function may also be screened against cells in cell-based assays, for example, to identify such compounds.

The invention also provides cell lines comprising nucleic acid sequences of the magnesium-dependent protein phosphatase gene. Such cell lines may be capable of expressing such sequences by virtue of operable linkage to a promoter functional in the cell line. Preferably, expression of the magnesium-dependent protein phosphatase gene sequence is under the control of an inducible promoter. Also provided are methods of identifying agents that interact with the magnesium-dependent protein phosphatase gene, comprising the steps of contacting the magnesium-dependent protein phosphatase gene with an agent and detecting an agent/magnesium-dependent protein phosphatase gene complex. Such complexes can be detected by, for example, measuring expression of an operably linked detectable marker.

The invention further provides methods of treating diseases or conditions associated with a disruption in the magnesium-dependent protein phosphatase gene, and more particularly, to a disruption in the expression or function of the magnesium-dependent protein phosphatase gene. In a preferred embodiment, methods of the present invention involve treating diseases or conditions associated with a disruption in the magnesium-dependent protein phosphatase gene's expression or function, including administering to a subject in need, a therapeutic agent that effects magnesium-dependent protein phosphatase expression or function. In accordance with this embodiment, the method comprises administration of a therapeutically effective amount of a natural, synthetic, semi-synthetic, or recombinant magnesium-dependent protein phosphatase gene, magnesium-dependent protein phosphatase gene products or fragments thereof as well as natural, synthetic, semi-synthetic or recombinant analogs.

The present invention further provides methods of treating diseases or conditions associated with disrupted targeted gene expression or function, wherein the methods comprise detecting and replacing through gene therapy mutated magnesium-dependent protein phosphatase genes.

Definitions

The term "gene" refers to (a) a gene containing at least one of the DNA sequences disclosed herein; (b) any DNA sequence that encodes the amino acid sequence encoded by the DNA sequences disclosed herein and/or; (c) any DNA sequence that hybridizes to the complement of the coding sequences disclosed herein. Preferably, the term includes coding as well as noncoding regions, and preferably includes all sequences necessary for normal gene expression including promoters, enhancers and other regulatory sequences.

The terms "polynucleotide" and "nucleic acid molecule" are used interchangeably to refer to polymeric forms of nucleotides of any length. The polynucleotides may contain deoxyribonucleotides, ribonucleotides and/or their analogs. Nucleotides may have any three-dimensional structure, and may perform any function, known or unknown. The term "polynucleotide" includes single-, double-stranded and triple helical molecules. "Oligonucleotide" refers to polynucleotides of between 5 and about 100 nucleotides of single- or double-stranded DNA. Oligonucleotides are also known as oligomers or oligos and may be isolated from genes, or chemically synthesized by methods known in the art. A "primer" refers to an oligonucleotide, usually single-stranded, that provides a 3'-hydroxyl end for the initiation of enzyme-mediated nucleic acid synthesis. The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A nucleic acid molecule may also comprise modified nucleic acid molecules, such as methylated nucleic acid molecules and nucleic acid molecule analogs. Analogs of purines and pyrimidines are known in the art, and include, but are not limited to, aziridinycytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudouracil, 5-pentylnyluracil and 2,6-diaminopurine. The use of uracil as a substitute for thymine in a deoxyribonucleic acid is also considered an analogous form of pyrimidine.

A "fragment" of a polynucleotide is a polynucleotide comprised of at least 9 contiguous nucleotides, preferably at least 15 contiguous nucleotides and more preferably at least 45 nucleotides, of coding or non-coding sequences.

The term "gene targeting" refers to a type of homologous recombination that occurs when a fragment of genomic DNA is introduced into a mammalian cell and that fragment locates and recombines with endogenous homologous sequences.

The term "homologous recombination" refers to the exchange of DNA fragments between two DNA molecules or chromatids at the site of homologous nucleotide sequences.

The term "homologous" as used herein denotes a characteristic of a DNA sequence having at least about 70 percent sequence identity as compared to a reference sequence, typically at least about 85 percent sequence identity, preferably at least about 95 percent sequence identity, and more preferably about 98 percent sequence identity, and most preferably about 100 percent sequence identity as compared to a reference sequence. Homology can be determined using a "BLASTN" algorithm. It is understood that homologous sequences can accommodate insertions, deletions and substitutions in the nucleotide sequence. Thus, linear sequences of nucleotides can be essentially identical even if some of the nucleotide residues do not precisely correspond or align. The reference sequence may be a subset of a larger sequence, such as a portion of a gene or flanking sequence, or a repetitive portion of a chromosome.

The term "target gene" (alternatively referred to as "target gene sequence" or "target DNA sequence" or "target sequence") refers to any nucleic acid molecule or polynucleotide of any gene to be modified by homologous recombination. The target sequence includes an intact gene, an exon or intron, a regulatory sequence or any region between genes. The target gene comprises a portion of a particular gene or genetic locus in the individual's genomic DNA. As provided herein, the target gene of the present invention is the magnesium-dependent protein phosphatase gene. A "magnesium-dependent protein phosphatase gene" refers to a sequence comprising SEQ ID NO:1 or comprising the magnesium-dependent protein phosphatase gene identified in Genebank as Accession No.: D28117; GI NO: 532678 and encoding a magnesium-dependent protein phosphatase, and more specifically, a magnesium-dependent protein phosphatase alpha or functional equivalent thereof. In one aspect, the coding sequence of the magnesium-dependent protein phosphatase gene comprises SEQ ID NO:1 or comprises the sequence identified in Genebank as Accession No.: D28117; GI NO: 532678 and encodes a magnesium-dependent protein phosphatase, and more specifically, a magnesium-dependent protein phosphatase alpha or a functional equivalent thereof.

"Disruption" of the magnesium-dependent protein phosphatase gene occurs when a fragment of genomic DNA locates and recombines with an endogenous homologous sequence. These sequence disruptions or modifications may include insertions, missense, frameshift, deletion, or substitutions, or magnesium-dependent protein phosphatasements of DNA sequence, or any combination thereof. Insertions include the insertion of entire genes, which may be of animal, plant, fungal, insect, prokaryotic, or viral origin. Disruption, for example, can alter or magnesium-dependent protein phosphatase a promoter, enhancer, or splice site of the magnesium-dependent protein phosphatase gene, and can alter the normal gene product by inhibiting its production partially or completely or by enhancing the normal gene product's activity.

The term, "transgenic cell", refers to a cell containing within its genome the magnesium-dependent protein phosphatase gene that has been disrupted, modified, altered, or magnesium-dependent protein phosphatased completely or partially by the method of gene targeting.

The term "transgenic animal" refers to an animal that contains within its genome a specific gene that has been disrupted by the method of gene targeting. The transgenic animal includes both the heterozygote animal (i.e., one defective allele and one wild-type allele) and the homozygous animal (i.e., two defective alleles). ). The term "transgenic mouse" or "transgenic mice" refers to a mouse or to mice containing within its genome a specific gene that has been disrupted by the method of gene targeting. The transgenic mouse includes both the heterozygote mouse (i.e., one defective allele and one wild-type allele) and the homozygous mouse (i.e., two defective alleles).

As used herein, the terms "selectable marker" or "positive selection marker" refers to a gene encoding a product that enables only the cells that carry the gene to survive and/or grow under certain conditions. For example, plant and animal cells that express the introduced neomycin resistance ($Neo^r$) gene are resistant to the compound G418. Cells that do not carry the $Neo^r$ gene marker are killed by G418. Other positive selection markers will be known to those of skill in the art.

A "host cell" includes an individual cell or cell culture that can be or has been a recipient for vector(s) or for incorporation of nucleic acid molecules and/or proteins. Host cells include progeny of a single host cell, and the progeny may not necessarily be completely identical (in morphology or in total DNA complement) to the original parent due to natural, accidental, or deliberate mutation. A host cell includes cells transfected with the constructs of the present invention.

The term "modulates" as used herein refers to the inhibition, reduction, increase or enhancement of the magnesium-dependent protein phosphatase function, expression, activity, or alternatively a phenotype associated with a disruption in the magnesium-dependent protein phosphatase gene.

The term "ameliorates" refers to a decreasing, reducing or eliminating of a condition, disease, disorder, or phenotype, including an abnormality or symptom associated with a disruption in the magnesium-dependent protein phosphatase gene.

The term "abnormality" refers to any disease, disorder, condition, or phenotype in which a disruption of the magnesium-dependent protein phosphatase gene is implicated, including pathological conditions.

BRIEF DESCRIPTION OF THE DRAWINGS

FIG. 1 shows the polynucleotide sequence for an orphan magnesium-dependent protein phosphatase(SEQ ID NO:1).

FIGS. 2A–2B show design of the targeting construct used to disrupt magnesium-dependent protein phosphatase genes. FIG. 2B shows the sequences identified as SEQ ID NO:3 and SEQ ID NO:4, which were used as the targeting arms (homologous sequences) in the magnesium-dependent protein phosphatase targeting construct.

DETAILED DESCRIPTION OF THE INVENTION

The invention is based, in part, on the evaluation of the expression and role of genes and gene expression products, primarily those associated with the magnesium-dependent protein phosphatase gene. Among others, the invention permits the definition of disease pathways and the identification of diagnostically and therapeutically useful targets. For example, genes that are mutated or down-regulated under disease conditions may be involved in causing or exacerbating the disease condition. Treatments directed at up-regulating the activity of such genes or treatments that involve alternate pathways, may ameliorate the disease condition.

Generation of Targeting Construct

The targeting construct of the present invention may be produced using standard methods known in the art. (See, e.g., Sambrook, et al., 1989, *Molecular Cloning: A Laboratory Manual*, Second Edition, Cold Spring Harbor Laboratory Press, Cold Spring Harbor, N.Y.; E. N. Glover (eds.), 1985, *DNA Cloning: A Practical Approach*, Volumes I and II; M. J. Gait (ed.), 1984, *Oligonucleotide Synthesis*; B. D. Hames & S. J. Higgins (eds.), 1985, Nucleic Acid Hybridization; B. D. Hames & S. J. Higgins (eds.), 1984, *Transcription and Translation*; R. I. Freshney (ed.), 1986, Animal Cell Culture; Immobilized Cells and Enzymes, IRL Press, 1986; B. Perbal, 1984, A Practical Guide To Molecular Cloning; F. M. Ausubel et al., 1994, *Current Protocols in Molecular Biology*, John Wiley & Sons, Inc.). For example, the targeting construct may be prepared in accordance with conventional ways, where sequences may be synthesized, isolated from natural sources, manipulated, cloned, ligated, subjected to in vitro mutagenesis, primer repair, or the like. At various stages, the joined sequences may be cloned, and analyzed by restriction analysis, sequencing, or the like.

The targeting DNA can be constructed using techniques well known in the art. For example, the targeting DNA may be produced by chemical synthesis of oligonucleotides, nick-translation of a double-stranded DNA template, polymerase chain-reaction amplification of a sequence (or ligase chain reaction amplification), purification of prokaryotic or target cloning vectors harboring a sequence of interest (e.g., a cloned cDNA or genomic DNA, synthetic DNA or from any of the aforementioned combination) such as plasmids, phagemids, YACs, cosmids, bacteriophage DNA, other viral DNA or replication intermediates, or purified restriction fragments thereof, as well as other sources of single and double-stranded polynucleotides having a desired nucleotide sequence. Moreover, the length of homology may be selected using known methods in the art. For example, selection may be based on the sequence composition and complexity of the predetermined endogenous target DNA sequence(s).

The targeting construct of the present invention typically comprises a first sequence homologous to a portion or region of the magnesium-dependent protein phosphatase gene and a second sequence homologous to a second portion or region of the magnesium-dependent protein phosphatase gene. The targeting construct further comprises a positive selection marker, which is preferably positioned in between the first and the second DNA sequence that are homologous to a portion or region of the target DNA sequence. The positive selection marker may be operatively linked to a promoter and a polyadenylation signal.

Other regulatory sequences known in the art may be incorporated into the targeting construct to disrupt or control expression of a particular gene in a specific cell type. In addition, the targeting construct may also include a sequence coding for a screening marker, for example, green fluorescent protein (GFP), or another modified fluorescent protein.

Although the size of the homologous sequence is not critical and can range from as few as 50 base pairs to as many as 100 kb, preferably each fragment is greater than about 1 kb in length, more preferably between about 1 and about 10 kb, and even more preferably between about 1 and about 5 kb. One of skill in the art will recognize that although larger fragments may increase the number of homologous recombination events in ES cells, larger fragments will also be more difficult to clone.

In a preferred embodiment of the present invention, the targeting construct is prepared directly from a plasmid genomic library using the methods described in pending U.S. patent application Ser. No. 08/971,310, filed Nov. 17, 1997, the disclosure of which is incorporated herein in its entirety. Generally, a sequence of interest is identified and isolated from a plasmid library in a single step using, for example, long-range PCR. Following isolation of this sequence, a second polynucleotide that will disrupt the target sequence can be readily inserted between two regions encoding the sequence of interest. In accordance with this aspect, the construct is generated in two steps by (1) amplifying (for example, using long-range PCR) sequences homologous to the target sequence, and (2) inserting another polynucleotide (for example a selectable marker) into the PCR product so that it is flanked by the homologous sequences. Typically, the vector is a plasmid from a plasmid genomic library. The completed construct is also typically a circular plasmid.

In another embodiment, the targeting construct is designed in accordance with the regulated positive selection method described in U.S. patent application Ser. No. 60/232,957, filed Sep. 15, 2000, the disclosure of which is incorporated herein in its entirety. The targeting construct is designed to include a PGK-neo fusion gene having two lacO sites, positioned in the PGK promoter and an NLS-lacI gene comprising a lac repressor fused to sequences encoding the NLS from the SV40 T antigen.

In another embodiment, the targeting construct may contain more than one selectable maker gene, including a negative selectable marker, such as the herpes simplex virus tk (HSV-tk) gene. The negative selectable marker may be operatively linked to a promoter and a polyadenylation signal. (See, e.g., U.S. Pat. Nos. 5,464,764; 5,487,992; 5,627,059; and 5,631,153).

Generation of Cells and Confirmation of Homologous Recombination Events

Once an appropriate targeting construct has been prepared, the targeting construct may be introduced into an appropriate host cell using any method known in the art. Various techniques may be employed in the present invention, including, for example, pronuclear microinjection; retrovirus mediated gene transfer into germ lines; gene targeting in embryonic stem cells; electroporation of embryos; sperm-mediated gene transfer; and calcium phosphate/DNA co-precipitates, microinjection of DNA into the nucleus, bacterial protoplast fusion with intact cells, transfection, polycations, e.g., polybrene, polyornithine, etc., or the like (See, e.g., U.S. Pat. No. 4,873,191; Van der Putten, et al., 1985, *Proc. Natl. Acad. Sci., USA* 82:6148–6152; Thompson, et al., 1989, *Cell* 56:313–321; Lo, 1983, *Mol Cell. Biol.* 3:1803–1814; Lavitrano, et al., 1989, *Cell*, 57:717–723). Various techniques for transforming mammalian cells are known in the art. (See, e.g., Gordon, 1989, *Intl. Rev. Cytol.*, 115:171–229; Keown et al., 1989, *Methods in Enzymology*; Keown et al., 1990, *Methods and Enzymology*, Vol. 185, pp. 527–537; Mansour et al., 1988, *Nature*, 336:348–352).

In a preferred aspect of the present invention, the targeting construct is introduced into host cells by electroporation. In this process, electrical impulses of high field strength reversibly permeabilize biomembranes allowing the introduction of the construct. The pores created during electroporation permit the uptake of macromolecules such as DNA. (See, e.g., Potter, H., et al., 1984, *Proc. Nat'l. Acad. Sci. U.S.A.* 81:7161–7165).

Any cell type capable of homologous recombination may be used in the practice of the present invention. Examples of such target cells include cells derived from vertebrates including mammals such as humans, bovine species, ovine species, murine species, simian species, and ether eucaryotic organisms such as filamentous fungi, and higher multicellular organisms such as plants.

Preferred cell types include embryonic stem (ES) cells, which are typically obtained from pre-implantation embryos cultured in vitro. (See, e.g., Evans, M. J., et al., 1981, *Nature* 292:154–156; Bradley, M. O., et al., 1984, *Nature* 309:255–258; Gossler et al., 1986, *Proc. Natl Acad. Sci. USA* 83:9065–9069; and Robertson, et al., 1986, *Nature* 322:445–448). The ES cells are cultured and prepared for introduction of the targeting construct using methods well known to the skilled artisan. (See, e.g., Robertson, E. J. ed. "Teratocarcinomas and Embryonic Stem Cells, a Practical Approach", IRL Press, Washington D.C., 1987; Bradley et al., 1986, *Current Topics in Devel. Biol.* 20:357–371; by Hogan et al. ,in "Manipulating the Mouse Embryo": A Laboratory Manual, Cold Spring Harbor Laboratory Press, Cold Spring Harbor N.Y., 1986; Thomas et al., 1987, *Cell* 51:503; Koller et al., 1991, *Proc. Natl. Acad. Sci. USA*, 88:10730; Dorin et al., 1992, *Transgenic Res.* 1:101; and Veis et al., 1993, *Cell* 75:229). The ES cells that will be inserted with the targeting construct are derived from an embryo or blastocyst of the same species as the developing embryo into which they are to be introduced. ES cells are typically selected for their ability to integrate into the inner cell mass and contribute to the germ line of an individual when introduced into the mammal in an embryo at the blastocyst stage of development. Thus, any ES cell line having this capability is suitable for use in the practice of the present invention.

The present invention may also be used to knockout genes in other cell types, such as stem cells. By way of example, stem cells may be myeloid, lymphoid, or neural progenitor and precursor cells. These cells comprising a disruption or knockout of a gene may be particularly useful in the study of magnesium-dependent protein phosphatase gene function in individual developmental pathways. Stem cells may be derived from any vertebrate species, such as mouse, rat, dog, cat, pig, rabbit, human, non-human primates and the like.

After the targeting construct has been introduced into cells, the cells where successful gene targeting has occurred are identified. Insertion of the targeting construct into the targeted gene is typically detected by identifying cells for expression of the marker gene. In a preferred embodiment, the cells transformed with the targeting construct of the present invention are subjected to treatment with an appropriate agent that selects against cells not expressing the selectable marker. Only those cells expressing the selectable marker gene survive and/or grow under certain conditions. For example, cells that express the introduced neomycin resistance gene are resistant to the compound G418, while cells that do not express the neo gene marker are killed by G418. If the targeting construct also comprises a screening marker such as GFP, homologous recombination can be identified through screening cell colonies under a fluorescent light. Cells that have undergone homologous recombination will have deleted the GFP gene and will not fluoresce.

If a regulated positive selection method is used in identifying homologous recombination events, the targeting construct is designed so that the expression of the selectable marker gene is regulated in a manner such that expression is inhibited following random integration but is permitted (derepressed) following homologous recombination. More particularly, the transfected cells are screened for expression of the neo gene, which requires that (1) the cell was successfully electroporated, and (2) lac repressor inhibition of neo transcription was relieved by homologous recombination. This method allows for the identification of transfected cells and homologous recombinants to occur in one step with the addition of a single drug.

Alternatively, a positive-negative selection technique may be used to select homologous recombinants. This technique involves a process in which a first drug is added to the cell population, for example, a neomycin-like drug to select for growth of transfected cells, i.e. positive selection. A second drug, such as FIAU is subsequently added to kill cells that express the negative selection marker, i.e. negative selection. Cells that contain and express the negative selection marker are killed by a selecting agent, whereas cells that do not contain and express the negative selection marker survive. For example, cells with non-homologous insertion of the construct express HSV thymidine kinase and therefore are sensitive to the herpes drugs such as gancyclovir (GANC) or FIAU (1-(2-deoxy 2-fluoro-B-D-arabinofluranosyl)-5-iodouracil). (See, e.g., Mansour et al., *Nature* 336:348–352: (1988); Capecchi, *Science* 244:1288–1292, (1989); Capecchi, *Trends in Genet.* 5:70–76 (1989)).

Successful recombination may be identified by analyzing the DNA of the selected cells to confirm homologous recombination. Various techniques known in the art, such as PCR and/or Southern analysis may be used to confirm homologous recombination events.

Homologous recombination may also be used to disrupt genes in stem cells, and other cell types, which are not totipotent embryonic stem cells. By way of example, stem cells may be myeloid, lymphoid, or neural progenitor and precursor cells. Such transgenic cells may be particularly useful in the study of magnesium-dependent protein phosphatase gene function in individual developmental pathways. Stem cells may be derived from any vertebrate species, such as mouse, rat, dog, cat, pig, rabbit, human, non-human primates and the like.

In cells that are not totipotent it may be desirable to knock out both copies of the target using methods that are known in the art. For example, cells comprising homologous recombination at a target locus that have been selected for expression of a positive selection marker (e.g., $Neo^r$) and screened for non-random integration, can be further selected for multiple copies of the selectable marker gene by exposure to elevated levels of the selective agent (e.g., G418). The cells are then analyzed for homozygosity at the target locus. Alternatively, a second construct can be generated with a different positive selection marker inserted between the two homologous sequences. The two constructs can be introduced into the cell either sequentially or simultaneously, followed by appropriate selection for each of the positive marker genes. The final cell is screened for homologous recombination of both alleles of the target.

Production of Transgenic Animals

Selected cells are then injected into a blastocyst (or other stage of development suitable for the purposes of creating a viable animal, such as, for example, a morula) of an animal (e.g., a mouse) to form chimeras (see e.g., Bradley, A. in *Teratocarcinomas and Embryonic Stem Cells: A Practical Approach*, E. J. Robertson, ed., IRL, Oxford, pp. 113–152 (1987)). Alternatively, selected ES cells can be allowed to aggregate with dissociated mouse embryo cells to form the aggregation chimera. A chimeric embryo can then be implanted into a suitable pseudopregnant female foster animal and the embryo brought to term. Chimeric progeny harbouring the homologously recombined DNA in their germ cells can be used to breed animals in which all cells of the animal contain the homologously recombined DNA. In one embodiment, chimeric progeny mice are used to generate a mouse with a heterozygous disruption in the magnesium-dependent protein phosphatase gene. Heterozygous transgenic mice can then be mated. It is well know in the art that typically ¼ of the offspring of such matings will have a homozygous disruption in the magnesium-dependent protein phosphatase gene.

The heterozygous and homozygous transgenic mice can then be compared to normal, wild type mice to determine whether disruption of the magnesium-dependent protein phosphatase gene causes phenotypic changes, especially pathological changes. For example, heterozygous and homozygous mice may be evaluated for phenotypic changes by physical examination, necropsy, histology, clinical chemistry, complete blood count, body weight, organ weights, and cytological evaluation of bone marrow.

In one embodiment, the phenotype (or phenotypic change) associated with a disruption in the magnesium-dependent protein phosphatase gene is placed into or stored in a database. Preferably, the database includes: (i) genotypic data (e.g., identification of the disrupted gene) and (ii) phenotypic data (e.g., phenotype(s) resulting from the gene disruption) associated with the genotypic data. The database is preferably electronic. In addition, the database is preferably combined with a search tool so that the database is searchable.

Conditional Transgenic Animals

The present invention further contemplates conditional transgenic or knockout animals, such as those produced using recombination methods. Bacteriophage P1 Cre recombinase and flp recombinase from yeast plasmids are two non-limiting examples of site-specific DNA recombinase enzymes that cleave DNA at specific target sites (lox P sites for cre recombinase and frt sites for flp recombinase) and catalyze a ligation of this DNA to a second cleaved site. A large number of suitable alternative site-specific recombinases have been described, and their genes can be used in accordance with the method of the present invention. Such recombinases include the Int recombinase of bacteriophage λ (with or without Xis) (Weisberg, R. et al., in *Lambda II*, (Hendrix, R., et al., Eds.), Cold Spring Harbor Press, Cold Spring Harbor, N.Y., pp. 211–50 (1983), herein incorporated by reference); TpnI and the β-lactamase transposons (Mercier, et al., *J. Bacteriol.*, 172:3745–57 (1990)); the Tn3 resolvase (Flanagan & Fennewald *J. Molec. Biol.*, 206:295–304 (1989); Stark, et al., *Cell*, 58:779–90 (1989)); the yeast recombinases (Matsuzaki, et al., *J. Bacteriol*., 172:610–18 (1990)); the *B. subtilis* SpoIVC recombinase (Sato, et al., *J. Bacteriol*. 172:1092–98 (1990)); the Flp recombinase (Schwartz & Sadowski, *J. Molec.Biol*., 205:647–658 (1989); Parsons, et al., *J. Biol. Chem*., 265:4527–33 (1990); Golic & Lindquist, *Cell*, 59:499–509 (1989); Amin, et al., *J. Molec. Biol*., 214:55–72 (1990)); the Hin recombinase (Glasgow, et al., *J. Biol. Chem*., 264:10072–82 (1989)); immunoglobulin recombinases (Malynn, et al., *Cell*, 54:453–460 (1988)); and the Cin recombinase (Haffter & Bickle, *EMBO J*., 7:3991–3996 (1988); Hubner, et al., *J. Molec. Biol*., 205:493–500 (1989)), all herein incorporated by reference. Such systems are discussed by Echols (*J. Biol. Chem*. 265:14697–14700 (1990)); de Villartay (*Nature*, 335:170–74 (1988)); Craig, (*Ann. Rev. Genet*., 22:77–105 (1988)); Poyart-Salmeron, et al., (*EMBO J*. 8:2425–33 (1989)); Hunger-Bertling, et al., (*Mol Cell. Biochem*., 92:107–16 (1990)); and Cregg & Madden (*Mol. Gen. Genet*., 219:320–23 (1989)), all herein incorporated by reference.

Cre has been purified to homogeneity, and its reaction with the loxP site has been extensively characterized (Abremski & Hess *J. Mol. Biol*. 259:1509–14 (1984), herein incorporated by reference). Cre protein has a molecular weight of 35,000 and can be obtained commercially from New England Nuclear/Du Pont. The cre gene (which encodes the Cre protein) has been cloned and expressed (Abremski, et al., *Cell* 32:1301–11 (1983), herein incorporated by reference). The Cre protein mediates recombination between two loxP sequences (Sternberg, et al., *Cold Spring Harbor Symp. Quant. Biol*. 45:297–309 (1981)), which may be present on the same or different DNA molecule. Because the internal spacer sequence of the loxP site is asymmetrical, two loxP sites can exhibit directionality relative to one another (Hoess & Abremski *Proc. Natl. Acad. Sci. U.S.A*. 81:1026–29 (1984)). Thus, when two sites on the same DNA molecule are in a directly repeated orientation, Cre will excise the DNA between the sites (Abremski, et al., *Cell* 32:1301–11 (1983)). However, if the sites are inverted with respect to each other, the DNA between them is not excised after recombination but is simply inverted. Thus, a circular DNA molecule having two loxP sites in direct orientation will recombine to produce two smaller circles, whereas circular molecules having two loxP sites in an inverted orientation simply invert the DNA sequences flanked by the loxP sites. In addition, recombinase action can result in reciprocal exchange of regions distal to the target site when targets are present on separate DNA molecules.

Recombinases have important application for characterizing gene function in knockout models. When the constructs described herein are used to disrupt magnesium-dependent protein phosphatase genes, a fusion transcript can be produced when insertion of the positive selection marker occurs downstream (3') of the translation initiation site of the magnesium-dependent protein phosphatase gene. The fusion transcript could result in some level of protein expression with unknown consequence. It has been suggested that insertion of a positive selection marker gene can affect the expression of nearby genes. These effects may make it difficult to determine gene function after a knockout event since one could not discern whether a given phenotype is associated with the inactivation of a gene, or the transcription of nearby genes. Both potential problems are solved by exploiting recombinase activity. When the positive selection marker is flanked by recombinase sites in the same orientation, the addition of the corresponding recombinase will result in the removal of the positive selection marker. In this way, effects caused by the positive selection marker or expression of fusion transcripts are avoided.

In one embodiment, purified recombinase enzyme is provided to the cell by direct microinjection. In another embodiment, recombinase is expressed from a co-transfected construct or vector in which the recombinase gene is operably linked to a functional promoter. An additional aspect of this embodiment is the use of tissue-specific or inducible recombinase constructs that allow the choice of when and where recombination occurs. One method for practicing the inducible forms of recombinase-mediated recombination involves the use of vectors that use inducible or tissue-specific promoters or other gene regulatory elements to express the desired recombinase activity. The inducible expression elements are preferably operatively positioned to allow the inducible control or activation of expression of the desired recombinase activity. Examples of such inducible promoters or other gene regulatory elements include, but are not limited to, tetracycline, metallothionine, ecdysone, and other steroid-responsive promoters, rapamycin responsive promoters, and the like (No, et al., *Proc. Natl. Acad. Sci. USA*, 93:3346–51 (1996); Furth, et al. ,*Proc. Natl. Acad. Sci. USA*, 91:9302–6 (1994)). Additional control elements that can be used include promoters requiring specific transcription factors such as viral, promoters. Vectors incorporating such promoters would only express recombinase activity in cells that express the necessary transcription factors.

Models for Disease

The cell- and animal-based systems described herein can be utilized as models for diseases. Animals of any species, including, but not limited to, mice, rats, rabbits, guinea pigs, pigs, micro-pigs, goats, and non-human primates, e.g., baboons, monkeys, and chimpanzees may be used to generate disease animal models. In addition, cells from humans may be used. These systems may be used in a variety of applications. Such assays may be utilized as part of screening strategies designed to identify agents, such as compounds that are capable of ameliorating disease symptoms. Thus, the animal- and cell-based models may be used to identify drugs, pharmaceuticals, therapies and interventions that may be effective in treating disease.

Cell-based systems may be used to identify compounds that may act to ameliorate disease symptoms. For example, such cell systems may be exposed to a compound suspected of exhibiting an ability to ameliorate disease symptoms, at a sufficient concentration and for a time sufficient to elicit such an amelioration of disease symptoms in the exposed cells. After exposure, the cells are examined to determine whether one or more of the disease cellular phenotypes has been altered to resemble a more normal or more wild type, non-disease phenotype.

In addition, animal-based disease systems, such as those described herein, may be used to identify compounds capable of ameliorating disease symptoms. Such animal models may be used as test substrates for the identification of drugs, pharmaceuticals, therapies, and interventions that may be effective in treating a disease or other phenotypic characteristic of the animal. For example, animal models may be exposed to a compound or agent suspected of exhibiting an ability to ameliorate disease symptoms, at a sufficient concentration and for a time sufficient to elicit such an amelioration of disease symptoms in the exposed animals. The response of the animals to the exposure may be monitored by assessing the reversal of disorders associated with the disease. Exposure may involve treating mother animals during gestation of the model animals described herein, thereby exposing embryos or fetuses to the compound or agent that may prevent or ameliorate the disease or phenotype. Neonatal, juvenile, and adult animals can also be exposed.

More particularly, using the animal models of the invention, specifically, transgenic mice, methods of identifying agents, including compounds are provided, preferably, on the basis of the ability to affect at least one phenotype associated with a disruption in the magnesium-dependent protein phosphatase gene. In one embodiment, the present invention provides a method of identifying agents having an effect on imagnesium-dependent protein phosphatase expression or function. The method includes measuring a physiological response of the animal, for example, to the agent, and comparing the physiological response of such animal to a control animal, wherein the physiological response of the animal comprising a disruption in the magnesium-dependent protein phosphatase as compared to the control animal indicates the specificity of the agent. A "physiological response" is any biological or physical parameter of an animal that can be measured. Molecular assays (e.g., gene transcription, protein production and degradation rates), physical parameters (e.g., exercise physiology tests, measurement of various parameters of respiration, measurement of heart rate or blood pressure, measurement of bleeding time, aPTT.T, or TT), and cellular assays (e.g.,. immunohistochemical assays of cell surface markers, or the ability of cells to aggregate or proliferate) can be used to assess a physiological response. The transgenic animals and cells of the present invention may be utilized as models for diseases, disorders, or conditions associated with phenotypes relating to a disruption in the magnesium-dependent protein phosphatase.

The present invention provides a unique animal model for testing and developing new treatments relating to the behavioral phenotypes. Analysis of the behavioral phenotype allows for the development of an animal model useful for testing, for instance, the efficacy of proposed genetic and pharmacological therapies for human genetic diseases, such as neurological, neuropsychological, or psychotic illnesses.

A statistical analysis of the various behaviors measured can be carried out using any conventional statistical program routinely used by those skilled in the art (such as, for example, "Analysis of Variance" or ANOVA). A "p" value of about 0.05 or less is generally considered to be statistically significant, although slightly higher p values may still be indicative of statistically significant differences. To statistically analyze abnormal behavior, a comparison is made between the behavior of a transgenic animal (or a group thereof) to the behavior of a wild-type mouse (or a group thereof), typically under certain prescribed conditions. "Abnormal behavior" as used herein refers to behavior exhibited by an animal having a disruption in the magnesium-dependent protein phosphatase gene, e.g. transgenic animal, which differs from an animal without a disruption in the magnesium-dependent protein phosphatase gene, e.g. wild-type mouse. Abnormal behavior consists of any number of standard behaviors that can be objectively measured (or observed) and compared. In the case of comparison, it is preferred that the change be statistically significant to confirm that there is indeed a meaningful behavioral difference between the knockout animal and the wild-type control animal. Examples of behaviors that may be measured or observed include, but are not limited to, ataxia, rapid limb movement, eye movement, breathing, motor activity, cognition, emotional behaviors, social behaviors, hyperactivity, hypersensitivity, anxiety, impaired learning, abnormal reward behavior, and abnormal social interaction, such as aggression.

A series of tests may be used to measure the behavioral phenotype of the animal models of the present invention, including neurological and neuropsychological tests to identify abnormal behavior. These tests may be used to measure abnormal behavior relating to, for example, learning and memory, eating, pain, aggression, sexual reproduction, anxiety, depression, schizophrenia, and drug abuse. (See, e.g., Crawley & Paylor, *Hormones and Behavior* 31:197–211 (1997)).

The social interaction test involves exposing a mouse to other animals in a variety of settings. The social behaviors of the animals (e.g., touching, climbing, sniffing, and mating) are subsequently evaluated. Differences in behaviors can then be statistically analyzed and compared (See, e.g., S. E. File, et al., *Pharmacol. Bioch. Behav.* 22:941–944 (1985); R. R. Holson, *Phys. Behav.* 37:239–247 (1986)). Examplary behavioral tests include the following.

The mouse startle response test typically involves exposing the animal to a sensory (typically auditory) stimulus and measuring the startle response of the animal (See, e.g., M. A. Geyer, et al., *Brain Res. Bull.* 25:485–498 (1990); Paylor and Crawley, *Psychopharmacology* 132:169–180 (1997)). A pre-pulse inhibition test can also be used, in which the percent inhibition (from a normal startle response) is measured by "cueing" the animal first with a brief low-intensity pre-pulse prior to the startle pulse.

The electric shock test generally involves exposure to an electrified surface and measurement of subsequent behaviors such as, for example, motor activity, learning, social behaviors. The behaviors are measured and statistically analyzed using standard statistical tests. (See, e.g., G. J. Kant, et al., *Pharm. Bioch. Behav.* 20:793–797 (1984); N. J. Leidenheimer, et al., *Pharmacol. Bioch. Behav.* 30:351–355 (1988)).

The tail-pinch or immobilization test involves applying pressure to the tail of the animal and/or restraining the animal's movements. Motor activity, social behavior, and cognitive behavior are examples of the areas that are measured. (See, e.g., M. Bertolucci D'Angic, et al., *Neurochem.* 55:1208–1214 (1990)).

The novelty test generally comprises exposure to a novel environment and/or novel objects. The animal's motor behavior in the novel environment and/or around the novel object are measured and statistically analyzed. (See, e.g., D. K. Reinstein, et al., *Pharm. Bioch. Behav.* 17:193–202 (1982); B. Poucet, *Behav. Neurosci.* 103:1009–10016 (1989); R. R. Holson, et al., *Phys. Behav.* 37:231–238 (1986)). This test may be used to detect visual processing deficiencies or defects.

The learned helplessness test involves exposure to stresses, for example, noxious stimuli, which cannot be affected by the animal's behavior. The animal's behavior can be statistically analyzed using various standard statistical tests. (See, e.g., A. Leshner, et al., *Behav. Neural Biol.* 26:497–501 (1979)).

Alternatively, a tail suspension test may be used, in which the "immobile" time of the mouse is measured when suspended "upside-down" by its tail. This is a measure of whether the animal struggles, an indicator of depression. In humans, depression is believed to result from feelings of a lack of control over one's life or situation. It is believed that a depressive state can be elicited in animals by repeatedly subjecting them to aversive situations over which they have no control. A condition of "learned helplessness" is eventually reached, in which the animal will stop trying to change its circumstances and simply accept its fate. Animals that stop struggling sooner are believed to be more prone to depression. Studies have shown that the administration of certain antidepressant drugs prior to testing increases the amount of time that animals struggle before giving up.

The Morris water-maze test comprises learning spatial orientations in water and subsequently measuring the animal's behaviors, such as, for example, by counting the number of incorrect choices. The behaviors measured are statistically analyzed using standard statistical tests. (See, e.g., E. M. Spruijt, et al., *Brain Res.* 527:192–197 (1990)).

Alternatively, a Y-shaped maze may be used (See, e.g., McFarland, D. J., *Pharmacology, Biochemistry and Behavior* 32:723–726 (1989); Dellu, F., et al., *Neurobiology of Learning and Memory* 73:31–48 (2000)). The Y-maze is generally believed to be a test of cognitive ability. The dimensions of each arm of the Y-maze can be, for example, approximately 40 cm×8 cm×20 cm, although other dimensions may be used. Each arm can also have, for example, sixteen equally spaced photobeams to automatically detect movement within the arms. At least two different tests can be performed using such a Y-maze. In a continuous Y-maze paradigm, mice are allowed to explore all three arms of a Y-maze for, e.g., approximately 10 minutes. The animals are continuously tracked using photobeam detection grids, and the data can be used to measure spontaneous alteration and positive bias behavior. Spontaneous alteration refers to the natural tendency of a "normal" animal to visit the least familiar arm of a maze. An alternation is scored when the animal makes two consecutive turns in the same direction, thus representing a sequence of visits to the least recently entered arm of the maze. Position bias determines egocentrically defined responses by measuring the animal's tendency to favor turning in one direction over another. Therefore, the test can detect differences in an animal's ability to navigate on the basis of allocentric or egocentric mechanisms. The two-trial Y-maze memory test measures response to novelty and spatial memory based on a free-choice exploration paradigm. During the first trial (acquisition), the animals are allowed to freely visit two arms of the Y-maze for, e.g., approximately 15 minutes. The third arm is blocked off during this trial. The second trial (retrieval) is performed after an intertrial interval of, e.g., approximately 2 hours. During the retrieval trial, the blocked arm is opened and the animal is allowed access to all three arms for, e.g., approximately 5 minutes. Data are collected during the retrieval trial and analyzed for the number and duration of visits to each arm. Because the three arms of the maze are virtually identical, discrimination between novelty and familiarity is dependent on "environmental" spatial cues around the room relative to the position of each arm. Changes in arm entry and duration of time spent in the novel arm in a transgenic animal model may be indicative of a role of that gene in mediating novelty and recognition processes.

The passive avoidance or shuttle box test generally involves exposure to two or more environments, one of which is noxious, providing a choice to be learned by the animal. Behavioral measures include, for example, response latency, number of correct responses, and consistency of response. (See, e.g., R. Ader, et al., *Psychon. Sci.* 26:125–128 (1972); R. R. Holson, *Phys. Behav.* 37:221–230 (1986)). Alternatively, a zero-maze can be used. In a zero-maze, the animals can, for example, be placed in a closed quadrant of an elevated annular platform having, e.g., 2 open and 2 closed quadrants, and are allowed to explore for approximately 5 minutes. This paradigm exploits an approach-avoidance conflict between normal exploratory activity and an aversion to open spaces in rodents. This test measures anxiety levels and can be used to evaluate the effectiveness of anti-anxiolytic drugs. The time spent in open quadrants versus closed quadrants may be recorded automatically, with, for example, the placement of photobeams at each transition site.

The food avoidance test involves exposure to novel food and objectively measuring, for example, food intake and intake latency. The behaviors measured are statistically analyzed using standard statistical tests. (See, e.g., B. A. Campbell, et al., *J. Comp. Physiol. Psychol.* 67:15–22 (1969)).

The elevated plus-maze test comprises exposure to a maze, without sides, on a platform, the animal's behavior is objectively measured by counting the number of maze entries and maze learning. The behavior is statistically analyzed using standard statistical tests. (See, e.g., H. A. Baldwin, et al., *Brain Res. Bull*, 20:603–606 (1988)).

The stimulant-induced hyperactivity test involves injection of stimulant drugs (e.g., amphetamines, cocaine, PCP, and the like), and objectively measuring, for example, motor activity, social interactions, cognitive behavior. The animal's behaviors are statistically analyzed using standard statistical tests. (See, e.g., P. B. S. Clarke, et al., *Psychopharmacology* 96:511–520 (1988); P. Kuczenski, et al., *J. Neuroscience* 11:2703–2712 (1991)).

The self-stimulation test generally comprises providing the mouse with the opportunity to regulate electrical and/or chemical stimuli to its own brain. Behavior is measured by frequency and pattern of self-stimulation. Such behaviors are statistically analyzed using standard statistical tests. (See, e.g., S. Nassif, et al., *Brain Res.*, 332:247–257 (1985); W. L. Isaac, et al., *Behav. Neurosci*. 103:345–355 (1989)).

The reward test involves shaping a variety of behaviors, e.g., motor, cognitive, and social, measuring, for example, rapidity and reliability of behavioral change, and statistically analyzing the behaviors measured. (See, e.g., L. E. Jarrard, et al., Exp. Brain Res. 61:519–530 (1986)).

The DRL (differential reinforcement to low rates of responding) performance test involves exposure to intermittent reward paradigms and measuring the number of proper responses, e.g., lever pressing. Such behavior is statistically analyzed using standard statistical tests. (See, e.g., J. D. Sinden, et al., Behav. Neurosci. 100:320–329 (1986); V. Nalwa, et al., Behav Brain Res. 17:73–76 (1985); and A. J. Nonneman, et al., J. Comp. Physiol. Psych. 95:588–602 (1981)).

The spatial learning test involves exposure to a complex novel environment, measuring the rapidity and extent of spatial learning, and statistically analyzing the behaviors measured. (See, e.g., N. Pitsikas, et al., Pharm. Bioch. Behav. 38:931–934 (1991); B. poucet, et al., Brain Res. 37:269–280 (1990); D. Christie, et al., Brain Res. 37:263–268 (1990); and F. Van Haaren, et al., Behav. Neurosci. 102:481–488 (1988)). Alternatively, an open-field (of) test may be used, in which the greater distance traveled for a given amount of time is a measure of the activity level and anxiety of the animal. When the open field is a novel environment, it is believed that an approach-avoidance situation is created, in which the animal is "torn" between the drive to explore and the drive to protect itself. Because the chamber is lighted and has no places to hide other than the corners, it is expected that a "normal" mouse will spend more time in the corners and around the periphery than it will in the center where there is no place to hide. "Normal" mice will, however, venture into the central regions as they explore more and more of the chamber. It can then be extrapolated that especially anxious mice will spend most of their time in the corners, with relatively little or no exploration of the central region, whereas bold (i.e., less anxious) mice will travel a greater distance, showing little preference for the periphery versus the central region.

The visual, somatosensory and auditory neglect tests generally comprise exposure to a sensory stimulus, objectively measuring, for example, orientating responses, and statistically analyzing the behaviors measured. (See, e.g., J. M. Vargo, et al., Exp. Neurol. 102:199–209 (1988)).

The consummatory behavior test generally comprises feeding and drinking, and objectively measuring quantity of consumption. The behavior measured is statistically analyzed using standard statistical tests. (See, e.g., P. J. Fletcher, et al., Psychopharmacol. 102:301–308 (1990); M. G. Corda, et al., Proc. Nat'l Acad. Sci. USA 80:2072–2076 (1983)).

A visual discrimination test can also be used to evaluate the visual processing of an animal. One or two similar objects are placed in an open field and the animal is allowed to explore for about 5–10 minutes. The time spent exploring each object (proximity to, i.e., movement within, e.g., about 3–5 cm of the object is considered exploration of an object) is recorded. The animal is then removed from the open field, and the objects are magnesium-dependent protein phosphatased by a similar object and a novel object. The animal is returned to the open field and the percent time spent exploring the novel object over the old object is measured (again, over about a 5–10 minute span). "Normal" animals will typically spend a higher percentage of time exploring the novel object rather than the old object. If a delay is imposed between sampling and testing, the memory task becomes more hippocampal-dependent. If no delay is imposed, the task is more based on simple visual discrimination. This test can also be used for olfactory discrimination, in which the objects (preferably, simple blocks) can be sprayed or otherwise treated to hold an odor. This test can also be used to determine if the animal can make gustatory discriminations; animals that return to the previously eaten food instead of novel food exhibit gustatory neophobia.

A hot plate analgesia test can be used to evaluate an animal's sensitivity to heat or painful stimuli. For example, a mouse can be placed on an approximately 55° C. hot plate and the mouse's response latency (e.g., time to pick up and lick a hind paw) can be recorded. These responses are not reflexes, but rather "higher" responses requiring cortical involvement. This test may be used to evaluate a nociceptive disorder.

An accelerating rotarod test may be used to measure coordination and balance in mice. Animals can be, for example, placed on a rod that acts like a rotating treadmill (or rolling log). The rotarod can be made to rotate slowly at first and then progressively faster until it reaches a speed of, e.g., approximately 60 rpm. The mice must continually reposition themselves in order to avoid falling off. The animals are preferably tested in at least three trials, a minimum of 20 minutes apart. Those mice that are able to stay on the rod the longest are believed to have better coordination and balance.

A metrazol administration test can be used to screen animals for varying susceptibilities to seizures or similar events. For example, a 5 mg/ml solution of metrazol can be infused through the tail vein of a mouse at a rate of, e.g., approximately 0.375 ml/min. The infusion will cause all mice to experience seizures, followed by death. Those mice that enter the seizure stage the soonest are believed to be more prone to seizures. Four distinct physiological stages can be recorded: soon after the start of infusion, the mice will exhibit a noticeable "twitch", followed by a series of seizures, ending in a final tensing of the body known as "tonic extension", which is followed by death.

Magnesium-dependent Protein Phosphatase Gene Products

The present invention further contemplates use of the magnesium-dependent protein phosphatase gene sequence to produce magnesium-dependent protein phosphatase gene products. magnesium-dependent protein phosphatase gene products may include proteins that represent functionally equivalent gene products. Such an equivalent gene product may contain deletions, additions or substitutions of amino acid residues within the amino acid sequence encoded by the gene sequences described herein, but which result in a silent change, thus producing a functionally equivalent magnesium-dependent protein phosphatase gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous gene products encoded by the magnesium-dependent protein phosphatase gene sequences. Alternatively, when utilized as part of an assay, "functionally equivalent" may refer to peptides capable of interacting with other cellular or extracellular molecules in a manner substantially similar to the way in which the corresponding portion of the endogenous gene product would.

Other protein products useful according to the methods of the invention are peptides derived from or based on the magnesium-dependent protein phosphatase gene produced by recombinant or synthetic means (derived peptides).

magnesium-dependent protein phosphatase gene products may be produced by recombinant DNA technology using techniques well known in the art. Thus, methods for preparing the gene polypeptides and peptides of the invention by expressing nucleic acid encoding gene sequences are described herein. Methods that are well known to those skilled in the art can be used to construct expression vectors containing gene protein coding sequences and appropriate transcriptional/translational control signals. These methods include, for example, in vitro recombinant DNA techniques, synthetic techniques and in vivo recombination/genetic recombination (See, e.g., Sambrook, et al., 1989, supra, and Ausubel, et al., 1989, supra). Alternatively, RNA capable of encoding gene protein sequences may be chemically synthesized using, for example, automated synthesizers (See, e.g. Oligonucleotide Synthesis: A Practical Approach, Gait, M. J. ed., IRL Press, Oxford (1984)).

A variety of host-expression vector systems may be utilized to express the gene coding sequences of the invention. Such host-expression systems represent vehicles by which the coding sequences of interest may be produced and subsequently purified, but also represent cells that may, when transformed or transfected with the appropriate nucleotide coding sequences, exhibit the gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing gene protein coding sequences; yeast (e.g. Saccharomyces, Pichia) transformed with recombinant yeast expression vectors containing the gene protein coding sequences; insect cell systems infected with recombinant virus expression vectors (e.g., baculovirus) containing the gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing gene protein coding sequences; or mammalian cell systems (e.g. COS, CHO, BHK, 293, 3T3) harboring recombinant expression constructs containing promoters derived from the genome of mammalian cells (e.g., metallothionine promoter) or from mammalian viruses (e.g., the adenovirus late promoter; the vaccinia virus 7.5 K promoter).

In bacterial systems, a number of expression vectors may be advantageously selected depending upon the use intended for the gene protein being expressed. For example, when a large quantity of such a protein is to be produced, for the generation of antibodies or to screen peptide libraries, for example, vectors that direct the expression of high levels of fusion protein products that are readily purified may be desirable. Such vectors include, but are not limited, to the *E. coli* expression vector pUR278 (Ruther et al., *EMBO J.*, 2:1791–94 (1983)), in which the gene protein coding sequence may be ligated individually into the vector in frame with the lac Z coding region so that a fusion protein is produced; pIN vectors (Inouye & Inouye, *Nucleic Acids Res.*, 13:3101–09 (1985); Van Heeke et al., *J. Biol. Chem.*, 264:5503–9 (1989)); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned magnesium-dependent protein phosphatase gene protein can be released from the GST moiety.

In a preferred embodiment, full length cDNA sequences are appended with inframe Bam HI sites at the amino terminus and Eco RI sites at the carboxyl terminus using standard PCR methodologies (Innis, et al. (eds) PCR Protocols: A Guide to Methods and Applications, Academic Press, San Diego (1990)) and ligated into the pGEX-2TK vector (Pharmacia, Uppsala, Sweden). The resulting cDNA construct contains a kinase recognition site at the amino terminus for radioactive labeling and glutathione Stransferase sequences at the carboxyl terminus for affinity purification (Nilsson, et al., *EMBO J.*, 4: 1075–80 (1985); Zabeau et al., *EMBO J.*, 1: 1217–24 (1982)).

In an insect system, *Autographa califomica* nuclear polyhedrosis virus (AcNPV) is used as a vector to express foreign genes. The virus grows in *Spodoptera frugiperda* cells. The gene coding sequence may be cloned individually into non-essential regions (for example the polyhedrin gene) of the virus and placed under control of an AcNPV promoter (for example the polyhedrin promoter). Successful insertion of gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (See, e.g., Smith, et al., *J. Virol.* 46: 584–93 (1983); U.S. Pat. No. 4,745,051).

In mammalian host cells, a number of viral-based expression systems may be utilized. In cases where an adenovirus is used as an expression vector, the gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing gene protein in infected hosts. (e.g., see Logan et al., *Proc. Natl. Acad. Sci. USA*, 81:3655–59 (1984)). Specific initiation signals may also be required for efficient translation of inserted gene coding sequences. These signals include the ATG initiation codon and adjacent sequences. In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter, et al., *Methods in Enzymol.*, 153:516–44 (1987)).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines that stably express the gene protein may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells that stably integrate the plasmid into their chromosomes and grow, to form foci, which in turn can be cloned and expanded into cell lines. This method may advantageously be used to engineer cell lines that express the gene protein. Such engineered cell lines may be particularly useful in screening and evaluation of compounds that affect the endogenous activity of the gene protein.

In a preferred embodiment, timing and/or quantity of expression of the recombinant protein can be controlled using an inducible expression construct. Inducible constructs and systems for inducible expression of recombinant proteins will be well known to those skilled in the art. Examples of such inducible promoters or other gene regulatory elements include, but are not limited to, tetracycline, metallothionine, ecdysone, and other steroid-responsive promoters, rapamycin responsive promoters, and the like (No, et al., *Proc. Natl. Acad. Sci. USA*, 93:3346–51 (1996); Furth, et al., *Proc. Natl. Acad. Sci. USA*, 91:9302–6 (1994)). Additional control elements that can be used include promoters requiring specific transcription factors such as viral, particularly HIV, promoters. In one in embodiment, a Tet inducible gene expression system is utilized. (Gossen et al., *Proc. Natl. Acad. Sci. USA*, 89:5547–51 (1992); Gossen, et al., *Science*, 268:1766–69 (1995)). Tet Expression Systems are based on two regulatory elements derived from the tetracycline-resistance operon of the *E. coli* Tn10 transposon—the tetracycline repressor protein (TetR) and the tetracycline operator sequence (tetO) to which TetR binds. Using such a system, expression of the recombinant protein is placed under the control of the tetO operator sequence and transfected or transformed into a host cell. In the presence of TetR, which is co-transfected into the host cell, expression of the recombinant protein is repressed due to binding of the TetR protein to the tetO regulatory element. High-level, regulated gene expression can then be induced in response to varying concentrations of tetracycline (Tc) or Tc derivatives such as doxycycline (Dox), which compete with tetO elements for binding to TetR. Constructs and materials for tet inducible gene expression are available commercially from CLONTECH Laboratories, Inc., Palo Alto, Calif.

When used as a component in an assay system, the gene protein may be labeled, either directly or indirectly, to facilitate detection of a complex formed between the gene protein and a test substance. Any of a variety of suitable labeling systems may be used including but not limited to radioisotopes such as $^{125}$I; enzyme labeling systems that generate a detectable calorimetric signal or light when exposed to substrate; and fluorescent labels. Where recombinant DNA technology is used to produce the gene protein for such assay systems, it may be advantageous to engineer fusion proteins that can facilitate labeling, immobilization and/or detection.

Indirect labeling involves the use of a protein, such as a labeled antibody, which specifically binds to the gene product. Such antibodies include but are not limited to polyclonal, monoclonal, chimeric, single chain, Fab fragments and fragments produced by a Fab expression library.

Production of Antibodies

Described herein are methods for the production of antibodies capable of specifically recognizing one or more epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of the magnesium-dependent protein phosphatase gene in a biological sample, or, alternatively, as a method for the inhibition of abnormal magnesium-dependent protein phosphatase gene activity. Thus, such antibodies may be utilized as part of disease treatment methods, and/or may be used as part of diagnostic techniques whereby patients may be tested for abnormal levels of magnesium-dependent protein phosphatase gene proteins, or for the presence of abnormal forms of such proteins.

For the production of antibodies, various host animals may be immunized by injection with the magnesium-dependent protein phosphatase gene, its expression product or a portion thereof. Such host animals may include but are not limited to rabbits, mice, rats, goats and chickens, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as magnesium-dependent protein phosphatase gene product, or an antigenic functional derivative thereof. For the production of polyclonal antibodies, host animals such as those described above, may be immunized by injection with gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to the hybridoma technique of K öhler and Milstein, *Nature*, 256:495–7 (1975); and U.S. Pat. No. 4,376,110), the human B-cell hybridoma technique (Kosbor, et al., *Immunology Today*, 4:72 (1983); Cote, et al., *Proc. Natl. Acad. Sci. USA*, 80:2026–30 (1983)), and the EBV-hybridoma technique (Cole, et al., in Monoclonal Antibodies And Cancer Therapy, Alan R. Liss, Inc., New York, pp. 77–96 (1985)). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., *Proc. Natl. Acad. Sci.*, 81:6851–6855 (1984); Takeda, et al., *Nature*, 314:452–54 (1985)) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, *Science* 242:423–26 (1988); Huston, et al., *Proc. Natl. Acad. Sci. USA*, 85:5879–83 (1988); and Ward, et al., *Nature*, 334:544–46 (1989)) can be adapted to produce gene-single chain antibodies. Single chain antibodies are typically formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments that can be produced by pepsin digestion of the antibody molecule and the Fab fragments that can be generated by reducing the disulfide bridges of the $F(ab')_2$ fragments. Alternatively, Fab expression libraries may be constructed (Huse, et al., *Science*, 246:1275–81 (1989)) to allow rapid and easy identification of monoclonal Fab fragments with the desired specificity.

Screening Methods

The present invention may be employed in a process for screening for agents such as agonists, i.e. agents that bind to and activate magnesium-dependent protein phosphatase polypeptides, or antagonists, i.e. inhibit the activity or interaction of magnesium-dependent protein phosphatase polypeptides with its ligand. Thus, polypeptides of the invention may also be used to assess the binding of small molecule substrates and ligands in, for example, cells, cell-free preparations, chemical libraries, and natural product mixtures as known in the art. Any methods routinely used to identify and screen for agents that can modulate receptors may be used in accordance with the present invention.

The present invention provides methods for identifying and screening for agents that modulate magnesium-dependent protein phosphatase expression or function. More particularly, cells that contain and express magnesium-dependent protein phosphatase gene sequences may be used to screen for therapeutic agents. Such cells may include non-recombinant monocyte cell lines, such as U937 (ATCC# CRL-1593), THP-1 (ATCC# TIB-202), and P388D1 (ATCC# TIB-63); endothelial cells such as HUVEC's and bovine aortic endothelial cells (BAEC's); as well as generic mammalian cell lines such as HeLa cells and COS cells, e.g., COS-7 (ATCC# CRL-1651). Further, such cells may include recombinant, transgenic cell lines. For example, the transgenic mice of the invention may be used to generate cell lines, containing one or more cell types involved in a disease, that can be used as cell culture models for that disorder. While cells, tissues, and primary cultures derived from the disease transgenic animals of the invention may be utilized, the generation of continuous cell lines is preferred. For examples of techniques that may be used to derive a continuous cell line from the transgenic animals, see Small, et al., *Mol. Cell Biol.*, 5:642–48 (1985).

magnesium-dependent protein phosphatase gene sequences may be introduced into, and overexpressed in, the genome of the cell of interest. In order to overexpress the magnesium-dependent protein phosphatase gene sequence, the coding portion of the magnesium-dependent protein phosphatase gene sequence may be ligated to a regulatory sequence that is capable of driving gene expression in the cell type of interest. Such regulatory regions will be well known to those of skill in the art, and may be utilized in the absence of undue experimentation. magnesium-dependent protein phosphatase gene sequences may also be disrupted or underexpressed. Cells having magnesium-dependent protein phosphatase gene disruptions or underexpressed magnesium-dependent protein phosphatase gene sequences may be used, for example, to screen for agents capable of affecting alternative pathways that compensate for any loss of function attributable to the disruption or underexpression.

In vitro systems may be designed to identify compounds capable of binding the magnesium-dependent protein phosphatase gene products. Such compounds may include, but are not limited to, peptides made of D-and/or L-configuration amino acids (in, for example, the form of random peptide libraries; (see e.g., Lam, et al., *Nature*, 354:82–4 (1991)), phosphopeptides (in, for example, the form of random or partially degenerate, directed phosphopeptide libraries; See, e.g., Songyang, et al., *Cell*, 72:767–78 (1993)), antibodies, and small organic or inorganic molecules. Compounds identified may be useful, for example, in modulating the activity of magnesium-dependent protein phosphatase gene proteins, preferably mutant magnesium-dependent protein phosphatase gene proteins; elaborating the biological function of the magnesium-dependent protein phosphatase gene protein; or screening for compounds that disrupt normal magnesium-dependent protein phosphatase gene interactions or themselves disrupt such interactions.

The principle of the assays used to identify compounds that bind to the magnesium-dependent protein phosphatase gene protein involves preparing a reaction mixture of the magnesium-dependent protein phosphatase gene protein and the test compound under conditions and for a time sufficient to allow the two components to interact and bind, thus forming a complex that can be removed and/or detected in the reaction mixture. These assays can be conducted in a variety of ways. For example, one method to conduct such an assay would involve anchoring the magnesium-dependent protein phosphatase gene protein or the test substance onto a solid phase and detecting target protein/test substance complexes anchored on the solid phase at the end of the reaction. In one embodiment of such a method, the magnesium-dependent protein phosphatase gene protein may be anchored onto a solid surface, and the test compound, which is not anchored, may be labeled, either directly or indirectly.

In practice, microtitre plates are conveniently utilized. The anchored component may be immobilized by non-covalent or covalent attachments. Non-covalent attachment may be accomplished simply by coating the solid surface with a solution of the protein and drying. Alternatively, an immobilized antibody, preferably a monoclonal antibody, specific for the protein may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for magnesium-dependent protein phosphatase gene product or the test compound to anchor any complexes formed in solution, and a labeled antibody specific for the other component of the possible complex to detect anchored complexes.

Compounds that are shown to bind to a particular magnesium-dependent protein phosphatase gene product through one of the methods described above can be further tested for their ability to elicit a biochemical response from the magnesium-dependent protein phosphatase gene protein. Agonists, antagonists and/or inhibitors of the expression product can be identified utilizing assays well known in the art.

Antisense, Ribozymes, and Antibodies

Other agents that may be used as therapeutics include the magnesium-dependent protein phosphatase gene, its expression product(s) and functional fragments thereof. Additionally, agents that reduce or inhibit mutant magnesium-dependent protein phosphatase gene activity may be used to ameliorate disease symptoms. Such agents include antisense, ribozyme, and triple helix molecules. Techniques for the production and use of such molecules are well known to those of skill in the art.

Anti-sense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the magnesium-dependent protein phosphatase gene nucleotide sequence of interest, are preferred.

Ribozymes are enzymatic RNA molecules capable of catalyzing the specific cleavage of RNA. The mechanism of ribozyme action involves sequence-specific hybridization of the ribozyme molecule to complementary target RNA, followed by an endonucleolytic cleavage. The composition of ribozyme molecules must include one or more sequences complementary to the magnesium-dependent protein phosphatase gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding magnesium-dependent protein phosphatase gene proteins.

Specific ribozyme cleavage sites within any potential RNA target are initially identified by scanning the molecule of interest for ribozyme cleavage sites that include the following sequences, GUA, GWU and GUC. Once identified, short RNA sequences of between 15 and 20 ribonucleotides corresponding to the region of the magnesium-dependent protein phosphatase gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules to be used in triple helix formation for the inhibition of transcription should be single stranded and composed of deoxyribonucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'–3', 3'–5' manner, such that they base pair with first one strand of a duplex and then the other, eliminating the necessity for a sizeable stretch of either purines or pyrimidines to be present on one strand of a duplex.

It is possible that the antisense, ribozyme, and/or triple helix molecules described herein may reduce or inhibit the transcription (triple helix) and/or translation (antisense, ribozyme) of mRNA produced by both normal and mutant magnesium-dependent protein phosphatase gene alleles. In order to ensure that substantially normal levels of magnesium-dependent protein phosphatase gene activity are maintained, nucleic acid molecules that encode and express magnesium-dependent protein phosphatase gene polypeptides exhibiting normal activity may be introduced into cells that do not contain sequences susceptible to whatever antisense, ribozyme, or triple helix treatments are being utilized. Alternatively, it may be preferable to coadminister normal magnesium-dependent protein phosphatase gene protein into the cell or tissue in order to maintain the requisite level of cellular or tissue magnesium-dependent protein phosphatase gene activity.

Anti-sense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Antibodies that are both specific for magnesium-dependent protein phosphatase gene protein, and in particular, mutant gene protein, and interfere with its activity may be used to inhibit mutant magnesium-dependent protein phosphatase gene function. Such antibodies may be generated against the proteins themselves or against peptides corresponding to portions of the proteins using standard techniques known in the art and as also described herein. Such antibodies include but are not limited to polyclonal, monoclonal, Fab fragments, single chain antibodies, chimeric antibodies, etc.

In instances where the magnesium-dependent protein phosphatase gene protein is intracellular and whole antibodies are used, internalizing antibodies may be preferred. However, lipofectin liposomes may be used to deliver the antibody or a fragment of the Fab region that binds to the magnesium-dependent protein phosphatase gene epitope into cells. Where fragments of the antibody are used, the smallest inhibitory fragment that binds to the target or expanded target protein's binding domain is preferred. For example, peptides having an amino acid sequence corresponding to the domain of the variable region of the antibody that binds to the magnesium-dependent protein phosphatase gene protein may be used. Such peptides may be synthesized chemically or produced via recombinant DNA technology using methods well known in the art (See, e.g., Creighton, Proteins: Structures and Molecular Principles (1984) W. H. Freeman, New York 1983, supra; and Sambrook, et al., 1989, supra). Alternatively, single chain neutralizing antibodies that bind to intracellular magnesium-dependent protein phosphatase gene epitopes may also be administered. Such single chain antibodies may be administered, for example, by expressing nucleotide sequences encoding single-chain antibodies within the target cell population by utilizing, for example, techniques such as those described in Marasco, et al., *Proc. Natl. Acad. Sci. USA*, 90:7889–93 (1993).

RNA sequences encoding magnesium-dependent protein phosphatase gene protein may be directly administered to a patient exhibiting disease symptoms, at a concentration sufficient to produce a level of magnesium-dependent protein phosphatase gene protein such that disease symptoms are ameliorated. Patients may be treated by gene magnesium-dependent protein phosphatasement therapy. One or more copies of a normal magnesium-dependent protein phosphatase gene, or a portion of the gene that directs the production of a normal magnesium-dependent protein phosphatase gene protein with magnesium-dependent protein phosphatase gene function, may be inserted into cells using vectors that include, but are not limited to adenovirus, adeno-associated virus, and retrovirus vectors, in addition to other particles that introduce DNA into cells, such as liposomes. Additionally, techniques such as those described above may be utilized for the introduction of normal magnesium-dependent protein phosphatase gene sequences into human cells.

Cells, preferably, autologous cells, containing normal magnesium-dependent protein phosphatase gene expressing gene sequences may then be introduced or reintroduced into the patient at positions that allow for the amelioration of disease symptoms.

Pharmaceutical Compositions, Effective Dosages, and Routes of Administration

The identified compounds that inhibit target mutant gene expression, synthesis and/or activity can be administered to a patient at therapeutically effective doses to treat or ameliorate the disease. A therapeutically effective dose refers to that amount of the compound sufficient to result in amelioration of symptoms of the disease.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, parenteral, topical, subcutaneous, intraperitoneal, intraveneous, intrapleural, intraoccular, intraarterial, or rectal administration. It is also contemplated that pharmaceutical compositions may be administered with other products that potentiate the activity of the compound and optionally, may include other therapeutic ingredients.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides. Oral ingestion is possibly the easiest method of taking any medication. Such a route of administration, is generally simple and straightforward and is frequently the least inconvenient or unpleasant route of administration from the patient's point of view. However, this involves passing the material through the stomach, which is a hostile environment for many materials, including proteins and other biologically active compositions. As the acidic, hydrolytic and proteolytic environment of the stomach has evolved efficiently to digest proteinaceous materials into amino acids and oligopeptides for subsequent anabolism, it is hardly surprising that very little or any of a wide variety of biologically active proteinaceous material, if simply taken orally, would survive its passage through the stomach to be taken up by the body in the small intestine. The result, is that many proteinaceous medicaments must be taken in through another method, such as parenterally, often by subcutaneous, intramuscular or intravenous injection.

Pharmaceutical compositions may also include various buffers (e.g., Tris, acetate, phosphate), solubilizers (e.g., Tween, Polysorbate), carriers such as human serum albumin, preservatives (thimerosol, benzyl alcohol) and anti-oxidants such as ascorbic acid in order to stabilize pharmaceutical activity. The stabilizing agent may be a detergent, such as tween-20, tween-80, NP-40 or Triton X-100. EBP may also be incorporated into particulate preparations of polymeric compounds for controlled delivery to a patient over an extended period of time. A more extensive survey of components in pharmaceutical compositions is found in Remington's Pharmaceutical Sciences, 18th ed., A. R. Gennaro, ed., Mack Publishing, Easton, Pa. (1990).

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

Diagnostics

A variety of methods may be employed to diagnose disease conditions associated with the magnesium-dependent protein phosphatase gene. Specifically, reagents may be used, for example, for the detection of the presence of magnesium-dependent protein phosphatase gene mutations, or the detection of either over or under expression of magnesium-dependent protein phosphatase gene mRNA.

According to the diagnostic and prognostic method of the present invention, alteration of the wild-type magnesium-dependent protein phosphatase gene locus is detected. In addition, the method can be performed by detecting the wild-type magnesium-dependent protein phosphatase gene locus and confirming the lack of a predisposition or neoplasia. "Alteration of a wild-type gene" encompasses all forms of mutations including deletions, insertions and point mutations in the coding and noncoding regions. Deletions may be of the entire gene or only a portion of the gene. Point mutations may result in stop codons, frameshift mutations or amino acid substitutions. Somatic mutations are those that occur only in certain tissues, e.g., in tumor tissue, and are not inherited in the germline. Germline mutations can be found in any of a body's tissues and are inherited. If only a single allele is somatically mutated, an early neoplastic state may be indicated. However, if both alleles are mutated, then a late neoplastic state may be indicated. The finding of gene mutations thus provides both diagnostic and prognostic information. A magnesium-dependent protein phosphatase gene allele that is not deleted (e.g., that found on the sister chromosome to a chromosome carrying the magnesium-dependent protein phosphatase gene deletion) can be screened for other mutations, such as insertions, small deletions, and point mutations. Mutations found in tumor tissues may be linked to decreased expression of the magnesium-dependent protein phosphatase gene product. However, mutations leading to non-functional gene products may also be linked to a cancerous state. Point mutational events may occur in regulatory regions, such as in the promoter of the gene, leading to loss or diminution of expression of the mRNA. Point mutations may also abolish proper RNA processing, leading to loss of expression of the magnesium-dependent protein phosphatase gene product, or a decrease in mRNA stability or translation efficiency.

One test available for detecting mutations in a candidate locus is to directly compare genomic target sequences from cancer patients with those from a control population. Alternatively, one could sequence messenger RNA after amplification, e.g., by PCR, thereby eliminating the necessity of determining the exon structure of the candidate gene. Mutations from cancer patients falling outside the coding region of the magnesium-dependent protein phosphatase gene can be detected by examining the non-coding regions, such as introns and regulatory sequences near or within the magnesium-dependent protein phosphatase gene. An early indication that mutations in noncoding regions are important may come from Northern blot experiments that reveal messenger RNA molecules of abnormal size or abundance in cancer patients as compared to control individuals.

The methods described herein may be performed, for example, by utilizing pre-packaged diagnostic kits comprising at least one specific gene nucleic acid or anti-gene antibody reagent described herein, which may be conveniently used, e.g., in clinical settings, to diagnose patients exhibiting disease symptoms or at risk for developing disease.

Any cell type or tissue, preferably platelets, neutrophils or lymphocytes, in which the gene is expressed may be utilized in the diagnostics described below.

DNA or RNA from the cell type or tissue to be analyzed may easily be isolated using procedures that are well known to those in the art. Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, PCR In Situ Hybridization: Protocols and Applications, Raven Press, N.Y. (1992)).

Gene nucleotide sequences, either RNA or DNA, may, for example, be used in hybridization or amplification assays of biological samples to detect disease-related gene structures and expression. Such assays may include, but are not limited to, Southern or Northern analyses, restriction fragment length polymorphism assays, single stranded conformational polymorphism analyses, in situ hybridization assays, and polymerase chain reaction analyses. Such analyses may reveal both quantitative aspects of the expression pattern of the gene, and qualitative aspects of the gene expression and/or gene composition. That is, such aspects may include, for example, point mutations, insertions, deletions, chromosomal rearrangements, and/or activation or inactivation of gene expression.

Preferred diagnostic methods for the detection of gene-specific nucleic acid molecules may involve for example, contacting and incubating nucleic acids, derived from the cell type or tissue being analyzed, with one or more labeled nucleic acid reagents under conditions favorable for the specific annealing of these reagents to their complementary sequences within the nucleic acid molecule of interest. Preferably, the lengths of these nucleic acid reagents are at least 9 to 30 nucleotides. After incubation, all non-annealed nucleic acids are removed from the nucleic acid:fingerprint molecule hybrid. The presence of nucleic acids from the fingerprint tissue that have hybridized, if any such molecules exist, is then detected. Using such a detection scheme, the nucleic acid from the tissue or cell type of interest may be immobilized, for example, to a solid support such as a membrane, or a plastic surface such as that on a microtitre plate or polystyrene beads. In this case, after incubation, non-annealed, labeled nucleic acid reagents are easily removed. Detection of the remaining, annealed, labeled nucleic acid reagents is accomplished using standard techniques well-known to those in the art.

Alternative diagnostic methods for the detection of gene-specific nucleic acid molecules may involve their amplification, e.g., by PCR (the experimental embodiment set forth in Mullis U.S. Pat. No. 4,683,202 (1987)), ligase chain reaction (Barany, *Proc. Natl. Acad. Sci. USA*, 88:189–93 (1991)), self sustained sequence replication (Guatelli, et al., *Proc. Natl. Acad. Sci. USA*, 87:1874–78 (1990)), transcriptional amplification system (Kwoh, et al., *Proc. Natl. Acad. Sci. USA*, 86:1173–77 (1989)), Q-Beta Replicase (Lizardi et al., *Bio/Technology*, 6:1197 (1988)), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment of such a detection scheme, a cDNA molecule is obtained from an RNA molecule of interest (e.g., by reverse transcription of the RNA molecule into cDNA). Cell types or tissues from which such RNA may be isolated include any tissue in which wild type fingerprint gene is known to be expressed, including, but not limited, to platelets, neutrophils and lymphocytes. A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method may be chosen from among the gene nucleic acid reagents described herein. The preferred lengths of such nucleic acid reagents are at least 15–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Antibodies directed against wild type or mutant gene peptides may also be used as disease diagnostics and prognostics. Such diagnostic methods, may be used to detect abnormalities in the level of gene protein expression, or abnormalities in the structure and/or tissue, cellular, or subcellular location of fingerprint gene protein. Structural differences may include, for example, differences in the size, electronegativity, or antigenicity of the mutant fingerprint gene protein relative to the normal fingerprint gene protein.

Protein from the tissue or cell type to be analyzed may easily be detected or isolated using techniques that are well known to those of skill in the art, including but not limited to western blot analysis. For a detailed explanation of methods for carrying out western blot analysis, see Sambrook, et al. (1989) supra, at Chapter 18. The protein detection and isolation methods employed herein may also be such as those described in Harlow and Lane, for example, (Antibodies: A Laboratory Manual, Cold Spring Harbor Laboratory Press, Cold Spring Harbor, N.Y. (1988)).

Preferred diagnostic methods for the detection of wild type or mutant gene peptide molecules may involve, for example, immunoassays wherein fingerprint gene peptides are detected by their interaction with an anti-fingerprint gene-specific peptide antibody.

For example, antibodies, or fragments of antibodies useful in the present invention may be used to quantitatively or qualitatively detect the presence of wild type or mutant gene peptides. This can be accomplished, for example, by immunofluorescence techniques employing a fluorescently labeled antibody (see below) coupled with light microscopic, flow cytometric, or fluorimetric detection. Such techniques are especially preferred if the fingerprint gene peptides are expressed on the cell surface.

The antibodies (or fragments thereof) useful in the present invention may, additionally, be employed histologically, as in immunofluorescence or immunoelectron microscopy, for in situ detection of fingerprint gene peptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fingerprint gene peptides, but also their distribution in the examined tissue. Using the present invention, those of ordinary skill will readily perceive that any of a wide variety of histological methods (such as staining procedures) can be modified in order to achieve such in situ detection.

Immunoassays for wild type, mutant, or expanded fingerprint gene peptides typically comprise incubating a biological sample, such as a biological fluid, a tissue extract, freshly harvested cells, or cells that have been incubated in tissue culture, in the presence of a detectably labeled antibody capable of identifying fingerprint gene peptides, and detecting the bound antibody by any of a number of techniques well known in the art.

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled gene-specific antibody. The solid phase support may then be washed with the buffer a second time to remove unbound antibody. The amount of bound label on solid support may then be detected by conventional means.

The terms "solid phase support or carrier" are intended to encompass any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild type or -mutant fingerprint gene peptide antibody may be determined according to well known methods. Those skilled in the art will be able to determine operative and optimal assay conditions for each determination by employing routine experimentation.

One of the ways in which the gene peptide-specific antibody can be detectably labeled is by linking the same to an enzyme and using it in an enzyme immunoassay (EIA) (Voller, *Ric Clin Lab*, 8:289–98 (1978) ["The Enzyme Linked Immunosorbent Assay (ELISA)", Diagnostic Horizons 2:1–7, 1978, Microbiological Associates Quarterly Publication, Walkersville, Md.]; Voller, et al., *J. Clin. Pathol.*, 31:507–20 (1978); Butler, *Meth. Enzymol.*, 73:482–523 (1981); Maggio (ed.), Enzyme Immunoassay, CRC Press, Boca Raton, Fla. (1980); Ishikawa, et al., (eds.) Enzyme Immunoassay, Igaku-Shoin, Tokyo (1981)). The enzyme that is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type, mutant, or expanded peptides through the use of a radioimmunoassay (RIA) (See, e.g., Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Throughout this application, various publications, patents and published patent applications are referred to by an identifying citation. The disclosures of these publications, patents and published patent specifications referenced in this application are hereby incorporated by reference into the present disclosure to more fully describe the state of the art to which this invention pertains.

The following examples are intended only to illustrate the present invention and should in no way be construed as limiting the subject invention.

EXAMPLES

Example 1

Targeting Construct for Magnesium-dependent Protein Phosphatase Gene

To investigate the role of genes encoding magnesium-dependent protein phosphatases, disruptions in genes comprising the sequence set forth in SEQ ID NO:1 were produced by homologous recombination. More particularly, as shown in FIGS. 2A–2B, a specific targeting construct having the ability to disrupt or modify genes, specifically comprising SEQ ID NO:1 was created using as the targeting arms (homologous sequences) in the construct, the sequences identified herein as SEQ ID NO:3 and SEQ ID NO:4.

Example 2

Generation of Transgenic Mice

The targeting construct was inserted into ES cells derived from the 129/OlaHsd mouse substrain by electroporation to generate chimeric mice. F1 mice were generated by breeding with C57BL/6 females. F2 homozygous mutant mice were produced by intercrossing F1 heterozygous males and females.

Example 3

Analysis of Transgenic Mice

The transgenic mice were analyzed for phenotypic changes as follows:

Necropsy. At necropsy, tissues were harvested and examined. The necropsy was performed following deep general anesthesia, cardiac puncture for terminal blood collection, and euthanasia. Body length and body weight were recorded for each mouse. The necropsy included a detailed examination of the whole mouse, the skinned carcass, skeleton, and all major organ systems. Lesions in organs and tissues were noted during the examination.

The transgenic mice at necropsy examination demonstrated patchy, red-yellow lung discoloration. The muscles and bones of the transgenic mice were softer than wild-type controls.

Histopathology. A histopathological examination of the transgenic mice was also conducted. Harvested organs were fixed in 10% neutral buffered formalin for a minimum of 48 hours at room temperature. Tissues were trimmed and samples taken to include the major features of each organ. Generally, if any abnormalities were noted at necropsy or at the time of tissue trimming, additional sample(s), if necessary, were taken to include the abnormalities so that it is available for microscopic analysis. Tissues were placed together, according to predetermined groupings, in tissue processing cassettes. All bones (and any calcified tissues) were decalcified with a formic acid or EDTA-based solution prior to trimming.

The infiltration of the tissues by paraffin was performed using an automated tissue processor. Steps in the cycle included dehydration through a graded series of ethanols, clearing using xylene or xylene substitute and infiltration with paraffin. Tissues were embedded in paraffin blocks with a standard orientation of specified tissues within each block. Sections were cut from each block at a thickness of 3–5 μm and mounted onto glass slides. After drying, the slides were stained with hematoxylin and eosin (H&E) and a glass coverslip was mounted over the sections. Generally, eighteen multi-tissue slides were prepared for each mouse. Phenotypically relevant lesions were extensively imaged along with wild-type littermate control images at the same magnifications, of the same structures/substructures.

Abnormalities in the lungs of the transgenic mice were found. More specifically, pulmonary lesions suggestive of foreign body aspiration pneumonia were detected. Patchy, peribronchial, acute inflammation with associated granulomata (probably foreign body), foamy alveolar macrophages, and eosinophilic crystals within alveolar macrophages were found in the lungs. Patchy yellow-red discoloration of the lungs was also detected.

Hematology. Blood samples were collected via a terminal cardiac puncture in a syringe. One hundred microliters of each whole blood sample were transferred into tubes pre-filled with EDTA. Approximately, 25 μL of the blood was placed onto a glass slide to prepare a peripheral blood smear. The blood smears were later stained with Wright's Stain that differentially stains white blood cell nuclei, granules and cytoplasm, and allows the identification of different cell types. The slides were analyzed microscopically by counting and noting each cell type in a total of 100 white blood cells. The percentage of each of the cell types counted was then calculated. Red blood cell morphology was also evaluated. The rest of the EDTA-anticoagulated whole blood sample was used to perform standard hematology tests. Whole blood was presently analyzed using a Cell-Dyn 3700 Hematology Analyzer. This instrument was calibrated for mouse blood parameters. Microscopic examinations of blood smears were performed to provide accurate differential blood leukocyte counts.

The transgenic mice demonstrated abnormalities in the blood that included an elevated white blood cell (WBC) count.

Behavior

Open Field Testing

Animals were group housed prior to testing. Each animal was placed gently in the center of its assigned chamber. Tests were for 10 minutes, with the experimenter out of the animals' sight. Immediately following the test session, the fecal boli was counted for each subject: increased boli was also an indication of anxiety. Activity of individual mice was recorded for the 10-minute test session and monitored by photobeam breaks in the x-, y- and z-axes. Measurements taken included total distance traveled, percent of session time spent in the central region of the test apparatus, and average velocity during the ambulatory episodes. Increases or decreases in total distance traveled over the test time may indicate hyperactivity or hypoactivity, respectively. Alterations in the regional distribution of movement may indicate anxiety phenotypes i.e., increased anxiety if there is a decrease in the time spent in the central region.

Homozygous mice displayed a statistically significant decrease in total time spent in the central region of the Open Field test. Specifically, when compared to age- and gender-matched wild-type control mice, homozygous mice spent significantly less time in the central region during the Open Field test. The data indicates that the mice displayed increased anxiety. This demonstrates that magnesium-dependent protein phosphatase may be an ideal small molecule target for an anti-anxiety drug, for example, agents that serve to upregulate the expression or activity of magnesium-dependent protein phosphatase or the protein itself may be used as a therapeutic to alleviate or ameliorate anxiety.

Hot Plate Testing

The hot plate analgesia test was designed to indicate an animal's sensitivity to a painful stimulus. The mouse was placed on a 55.5° C. hot plate, and latency of the mouse to pick up and lick or fan a hindpaw was recorded. Specifically, adult wild-type and homozygous mice were placed on a hot plate surface preheated to 55.5° C. one at a time. A built-in timer was started as soon as the subjects were placed on the hot plate surface. The timer was stopped the instant the animal lifted its paw from the plate, reacting to the discomfort. Animal reaction time was a measurement of the animal's resistance to pain. The time points to hindpaw licking or fanning, up to a 60-second maximum, was recorded. Once the behavior was observed, the animal was immediately removed from the hot plate to prevent discomfort or injury.

Also, there was a significant difference detected during Hot Plate testing. The mean for the homozygous mutants to lick or fan their hindpaw was significantly increased compared to wild-type littermates, demonstrating increased pain threshold. Three mice out of the 16 mutant mice tested were "non-responders" and never licked their hindpaw during the 60 second test period.

Example 4

Expression Analysis

Gene expression analysis was conducted on all targets using a knocked-in lacZ as a reporter gene.

LacZ: In general, tissues from heterozygous mutant mice were frozen, sectioned (10 μm), stained and analyzed for lacZ expression using X-Gal as a substrate for beta-galactosidase, followed by a Nuclear Fast Red counterstaining. In addition, brain wholemount staining was performed.

The dissected brain was cut longitudinally, fixed and stained using X-Gal as the substrate for beta-galactosidase. The reaction was stopped by washing the brain in PBS and then fixed in PBS-buffered formaldehyde.

Wild-type control tissues were also stained for lacZ expression to reveal any background or signals due to endogenous beta-galactosidase activity. The following tissues can show staining in the wild-type control sections and were therefore not suitable for X-gal staining: small and large intestines, stomach, vas deferens and epididymis. It was reported that these organs contain high levels of endogenous beta-galactosidase activity. Heterozygous mice at two weeks were analyzed for lacZ expression.

In the transgenic mice of the present invention, strong lacZ expression was detectable in all tissue or organs examined, including the brain, spinal cord, sciatic nerve, eyes, harderian glands, thymus, spleen, lymph nodes, bone marrow, aorta, heart, lung, liver, gallbladder, pancreas, kidney, urinary bladder, trachea, larynx, esophagus, thyroid gland, pituitary gland, adrenal gland, salivary gland, tongue, skeletal muscle, skin, and female and male reproductive systems.

As is apparent to one of skill in the art, various modifications of the above embodiments can be made without departing from the spirit and scope of this invention. These modifications and variations are within the scope of this invention.

I claim:

1. A transgenic mouse comprising a disruption in a magnesium-dependent protein phosphatase gene represented by SEQ ID NO: 1, wherein where the disruption is homozygous the transgenic mouse lacks production of functional protein encoded by the magnesium-dependent protein phosphatase gene and the transgenic mouse exhibits, relative to a wild-type mouse, a phenotypic abnormality selected from the group consisting of a lung abnormality, elevated white blood cell count, increased anxiety and increased pain threshold.

2. A cell isolated from the transgenic mouse of claim 1.

3. A method of producing a transgenic mouse comprising a homozygous disruption in a magnesium-dependent protein phosphatase gene represented by SEQ ID NO:1, the method comprising:

(a) introducing a targeting construct capable of disrupting the magnesium-dependent protein phosphatase gene represented by SEQ ID NO:1 into a mouse embryonic stem cell;

(b) selecting for a mouse embryonic stem cell comprising a disruption in the magnesium-dependent protein phosphatase gene;

(c) introducing the embryonic stem cell selected for in step (b) into a blastocyst;

(d) implanting the resulting blastocyst into a pseudopregnant mouse, wherein said mouse gives birth to a chimeric mouse;

(e) breeding the chimeric mouse to produce a transgenic mouse comprising a heterozygous disruption in the magnesium-dependent protein phosphatase gene; and (f) breeding the heterozygous transgenic mouse of step (e) to produce a transgenic mouse comprising a homozygous disruption in the magnesium-dependent phosphatase gene represented by SEQ ID NO:1, wherein the transgenic mouse when homozygous for the disruption lacks production of functional protein encoded by the magnesium-dependent protein phosphatase gene and the transgenic mouse exhibits, relative to a wild-type mouse, a phenotypic abnormality selected from the group consisting of a lung abnormality, elevated white blood cell count, increased anxiety and increased pain threshold.

4. The transgenic mouse of claim 1, wherein the lung abnormality comprises pulmonary lesions.

5. The transgenic mouse of claim 4, wherein the pulmonary lesions are consistent with a symptom associated with pneumonia.

6. The transgenic mouse of claim 1, wherein the increased anxiety is characterized by a decreased amount of time spent in a central region during an open field test.

7. The transgenic mouse of claim 1, wherein the increased pain threshold is characterized by an increased response latency during a hot plate test.

* * * * *

SEQUENCE LISTING

<160> NUMBER OF SEQ ID NOS: 4

<210> SEQ ID NO 1
<211> LENGTH: 1387
<212> TYPE: DNA
<213> ORGANISM: Mus musculus

<400> SEQUENCE: 1

```
cccgggcccg gccgccgtcg cgggaccccg tgcccggccg ccgtcgccac cgccgccccg     60
gccgaccgag ggacccgccc gcccgcggct gctccggacc tagaggatca agtcataatg    120
ggagcatttt tagacaagcc aaagatggag aagcataatg cccaggggca ggggaatggg    180
ttacgatacg gcctaagcag catgcaaggt tggcgagttg aaatggagga cgcacacacg    240
gctgtgatcg gtttgccaag tggacttgag acatggtcat tctttgctgt atatgatggg    300
catgctggtt ctcaggttgc caaatactgc tgtgagcact tgttagatca catcaccaat    360
aaccaggatt tcagaggatc tgcaggagca ccttctgtgg agaacgtaaa gaatggaatc    420
agaacagggt ttctggagat tgatgaacac atgagagtta tgtcagagaa gaaacatggt    480
gcagatagaa gcgggtcaac agctgtgggc gtcttaatct ctccccaaca tacttatttc    540
attaactgtg gagactcgag aggtttactt tgtaggaata gaaaagttca cttcttcaca    600
caagaccata aaccaagtaa cccgctggaa aaagaacgaa ttcagaatgc agggggctcg    660
gtgatgattc agcgtgtcaa tggctctctg gctgtatcga gggcccttgg ggatttcgat    720
tacaaatgtg tccatggaaa aggtcccaca gagcagcttg tctccccaga gcccgaagtc    780
catgatattg aaaggtctga agaagatgac cagttcatca tccttgcatg cgatggcatc    840
tgggacgtca tggggaacga agagctctgt gactttgtga gatccagact tgaagtcact    900
gatgaccttg agaaagtttg caatgaagta gtcgacacct gcttgtataa gggaagtcga    960
gacaacatga gtgtgatttt gatctgtttt ccaagtgcac ccaaagtctc ggcagaggcg   1020
gtgaagaagg aggcggagct ggacaagtac ctggagagca gagtagaaga aatcataaag   1080
aagcaggtgg aaggcgtccc tgacttagtc cacgtgatgc gcacgttagc cagtgagaac   1140
atccccagcc tcccaccagg gggtgaattg gcaagcaagc ggaatgtaat tgaagccgtt   1200
tacaatagac tgaaccctta caaaaatgac gacactgatt ctgcgtcaac cgatgatatg   1260
tggtaaagcc gctcacccag ccgtggactc accttcgcct gcaaagggga agccagctca   1320
tccttgccga gcctttacca tccatcaccg acttcacagg agggtctgac acgggtgagg   1380
actgcag                                                             1387
```

<210> SEQ ID NO 2

-continued

```
<211> LENGTH: 382
<212> TYPE: PRT
<213> ORGANISM: Mus musculus

<400> SEQUENCE: 2

Met Gly Ala Phe Leu Asp Lys Pro Lys Met Glu Lys His Asn Ala Gln
 1               5                  10                  15

Gly Gln Gly Asn Gly Leu Arg Tyr Gly Leu Ser Ser Met Gln Gly Trp
            20                  25                  30

Arg Val Glu Met Glu Asp Ala His Thr Ala Val Ile Gly Leu Pro Ser
        35                  40                  45

Gly Leu Glu Thr Trp Ser Phe Phe Ala Val Tyr Asp Gly His Ala Gly
    50                  55                  60

Ser Gln Val Ala Lys Tyr Cys Cys Glu His Leu Leu Asp His Ile Thr
65                  70                  75                  80

Asn Asn Gln Asp Phe Arg Gly Ser Ala Gly Ala Pro Ser Val Glu Asn
                85                  90                  95

Val Lys Asn Gly Ile Arg Thr Gly Phe Leu Glu Ile Asp Glu His Met
            100                 105                 110

Arg Val Met Ser Glu Lys Lys His Gly Ala Asp Arg Ser Gly Ser Thr
        115                 120                 125

Ala Val Gly Val Leu Ile Ser Pro Gln His Thr Tyr Phe Ile Asn Cys
    130                 135                 140

Gly Asp Ser Arg Gly Leu Leu Cys Arg Asn Arg Lys Val His Phe Phe
145                 150                 155                 160

Thr Gln Asp His Lys Pro Ser Asn Pro Leu Glu Lys Glu Arg Ile Gln
                165                 170                 175

Asn Ala Gly Gly Ser Val Met Ile Gln Arg Val Asn Gly Ser Leu Ala
            180                 185                 190

Val Ser Arg Ala Leu Gly Asp Phe Asp Tyr Lys Cys Val His Gly Lys
        195                 200                 205

Gly Pro Thr Glu Gln Leu Val Ser Pro Glu Pro Glu Val His Asp Ile
    210                 215                 220

Glu Arg Ser Glu Glu Asp Asp Gln Phe Ile Ile Leu Ala Cys Asp Gly
225                 230                 235                 240

Ile Trp Asp Val Met Gly Asn Glu Glu Leu Cys Asp Phe Val Arg Ser
                245                 250                 255

Arg Leu Glu Val Thr Asp Asp Leu Glu Lys Val Cys Asn Glu Val Val
            260                 265                 270

Asp Thr Cys Leu Tyr Lys Gly Ser Arg Asp Asn Met Ser Val Ile Leu
        275                 280                 285

Ile Cys Phe Pro Ser Ala Pro Lys Val Ser Ala Glu Ala Val Lys Lys
    290                 295                 300

Glu Ala Glu Leu Asp Lys Tyr Leu Glu Ser Arg Val Glu Glu Ile Ile
305                 310                 315                 320

Lys Lys Gln Val Glu Gly Val Pro Asp Leu Val His Val Met Arg Thr
                325                 330                 335

Leu Ala Ser Glu Asn Ile Pro Ser Leu Pro Pro Gly Gly Glu Leu Ala
            340                 345                 350

Ser Lys Arg Asn Val Ile Glu Ala Val Tyr Asn Arg Leu Asn Pro Tyr
        355                 360                 365

Lys Asn Asp Asp Thr Asp Ser Ala Ser Thr Asp Asp Met Trp
    370                 375                 380
```

-continued

```
<210> SEQ ID NO 3
<211> LENGTH: 200
<212> TYPE: DNA
<213> ORGANISM: Artificial Sequence
<220> FEATURE:
<223> OTHER INFORMATION: Targeting vector

<400> SEQUENCE: 3

gcaacacaat gcttgtaggt atagcctgtg agtttttcca gcttccttgt atcttataga     60

ttctgggtaa agagtgttgg acatgttttg tttcaaaggc aatcacttat tttcttattt    120

ctcttccttt acagacctag aggatcaagt cataatggga gcatttttag acaagccaaa    180

gatggagaag cataatgccc                                                200


<210> SEQ ID NO 4
<211> LENGTH: 200
<212> TYPE: DNA
<213> ORGANISM: Artificial Sequence
<220> FEATURE:
<223> OTHER INFORMATION: Targeting vector

<400> SEQUENCE: 4

ctgctgtgag cacttgttag atcacatcac caataaccag gatttcagag gatctgcagg     60

agcaccttct gtggagaacg taaagaatgg aatcagaaca gggtttctgg agattgatga    120

acacatgaga gttatgtcag agaagaaaca tggtgcagat agaagcgggt caacagctgt    180

gggcgtctta atctctcccc                                                200
```